United States Patent
Follmann et al.

(10) Patent No.: US 8,420,656 B2
(45) Date of Patent: Apr. 16, 2013

(54) SUBSTITUTED 5-FLUORO-1H-PYRAZOLOPYRIDINES AND THEIR USE

(75) Inventors: Markus Follmann, Wülfrath (DE); Johannes-Peter Stasch, Solingen (DE); Gorden Redlich, Bochum (DE); Jens Ackerstaff, Düsseldorf (DE); Nils Griebenow, Dormagen (DE); Walter Kroh, Wuppertal (DE); Andreas Knorr, Erkrath (DE); Eva-Maria Becker, Wuppertal (DE); Frank Wunder, Wuppertal (DE); Volkhart Min-Jian Li, Velbert (DE); Elke Hartmann, Wuppertal (DE); Joachim Mittendorf, Wuppertal (DE); Karl-Heinz Schlemmer, Wuppertal (DE); Rolf Jautelat, Haan (DE); Donald Bierer, Haan (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/111,856

(22) Filed: May 19, 2011

(65) Prior Publication Data

US 2012/0022084 A1    Jan. 26, 2012

(30) Foreign Application Priority Data

May 26, 2010 (DE) .......................... 10 2010 021637

(51) Int. Cl.
*A01N 43/54* (2006.01)
*C07D 239/42* (2006.01)
*C07D 401/04* (2006.01)

(52) U.S. Cl.
USPC .......................................... 514/256; 544/296

(58) Field of Classification Search .................. 544/296; 514/256
See application file for complete search history.

(56) References Cited

U.S. PATENT DOCUMENTS

| | | | |
|---|---|---|---|
| 6,180,656 B1 | 1/2001 | Furstner et al. | |
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,903,089 B1 | 6/2005 | Stasch et al. | |
| 7,105,523 B2 | 9/2006 | Stasch et al. | |
| 7,173,037 B2 * | 2/2007 | Alonso-Alija et al. | 514/256 |
| 7,317,016 B2 | 1/2008 | Stasch et al. | |
| 7,427,617 B2 | 9/2008 | Feurer et al. | |
| 2004/0171832 A1 | 9/2004 | Stasch et al. | |
| 2004/0235863 A1 | 11/2004 | Feurer et al. | |
| 2006/0052397 A1 | 3/2006 | Alonso-Alija et al. | |
| 2010/0029653 A1 | 2/2010 | Schirok et al. | |
| 2010/0184980 A1 | 7/2010 | Jimenez et al. | |
| 2011/0245273 A1 * | 10/2011 | Schirok et al. | 514/256 |

FOREIGN PATENT DOCUMENTS

| | | |
|---|---|---|
| CA | 2127624 | 1/1995 |
| CA | 2577420 | 3/2006 |
| CN | 1613849 | 5/2005 |
| WO | 03076408 | 9/2003 |
| WO | WO 03095451 A1 * | 11/2003 |

OTHER PUBLICATIONS

Mittendorf et al., "Discovery of Riociguat (BAY 63-2521): A Potent, Oral Stimulator of Soluble Guanylate Cyclase for the Treatment of Pulmonary Hypertension," Chem Med Chem, 2009, No. 4, 853-865.
Ko et al., "YC-1, a Novel Activator of Platelet Guanylate Cyclase;" Blood, 1994, 84, pp. 4226-4233.
Mülsch et al., "Effect of YC-1, an NO-independent, Superoxide-Sensitive Stimulaotr of Soluble Gyanylyl Cyclase, on Smooth Muscle Responsiveness to Nitrovasodilators;" Brit. J. Pharm., 1997, 120, pp. 681-689.
Goldberg et al., "Stimulation of Human Platelet Guanylate Cyclase by Fatty Acids," J. Biol. Chem., 1977, 252, pp. 1279-1285.
Pettibone et al., "A Structurally Novel Stimulator of Guanylate Cyclase with Long-Lasting Hypotensive Activity in the Dog," Euro. J. of Pharmacology, 1985, 116, pp. 307-312.
Yu et al., "Vasorelaxant Effect of Isoliquiritigenin, A Novel Soluble Guanylate Cyclase Activator, in Rat Aorta," Brit. J. of Pharmacology, 1995, 114, pp. 1587-1594.
Hajos, et al., "Product Class 5: Azaindolizines with two nitrogen atoms in the five-membered ring," Science of Synthesis, 2002, vol. 12, pp. 613-678 Georg Thieme Verlag, Stuttgart, New York.
Wunder, et al., A cell-based cGMP assay useful for ultra-high-throughput screening and identification of modulators of the nitric oxide/cGMP pathway, Anal. Biochem., 2005, 339, 104-112.
Hassan, et al., Aryl-Aryl Bond Formation One Century after the Discovery of the Ullmann Reaction, Chem. Rev. 2002, 102, 1359-1469.
English Abstract of CN 1613849, listed above, (May 5, 2005).
U.S. Appl. No. 12/299,906, filed May 18, 2009.
U.S. Appl. No. 12/441,242, filed Mar. 13, 2009.
U.S. Appl. No. 13/133,383, filed Jun. 7, 2011.
U.S. Appl. No. 13/143,415, filed Sep. 16, 2011.

\* cited by examiner

*Primary Examiner* — James O Wilson
*Assistant Examiner* — Alexander R Pagano
(74) *Attorney, Agent, or Firm* — Karen B. King

(57) ABSTRACT

The present application relates to novel substituted 5-fluoro-1H-pyrazolopyridines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

7 Claims, No Drawings

SUBSTITUTED 5-FLUORO-1H-PYRAZOLOPYRIDINES AND THEIR USE

This application claims the benefit of priority of German Application Number DE 10201002637.2, filed May 26, 2010.

The present application relates to novel substituted 5-fluoro-1H-pyrazolopyridines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyze the biosynthesis of cGMP from guanosine triphosphate (GTP). The known representatives of this family can be classified both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. It is of central importance for the activation mechanism. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disturbance of the abovementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

Owing to the expected high efficiency and few side effects, a treatment of such disorders which targets the influence of the cGMP signal path in organisms and is NO-independent is a promising approach.

Hitherto, for the therapeutic stimulation of the soluble guanylate cyclase use has exclusively been made of compounds such as organic nitrates whose effect is based on NO. This is formed by bioconversion and activates soluble guanylate cyclase by attack at the central iron atom of haem. In addition to the side effects, the development of tolerance is one of the decisive disadvantages of this type of treatment.

In recent years, some substances have been described which stimulate soluble guanylate cyclase directly, i.e. without prior release of NO, such as, for example 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

WO 00/06569 discloses fused pyrazole derivatives and WO 03/095451 carbamate-substituted 3-pyrimidinylyrazolopyridines as stimulators of soluble guanylate cyclase.

It is an object of the present invention to provide novel substances which act as stimulators of soluble guanylate cyclase and which have an identical or improved therapeutic profile compared to compounds known from the prior art, such as, for example, with respect to their in vivo properties such as, for example, their pharmacokinetic and pharmacodynamic behaviour and/or their dose-activity relationship.

The present invention provides compounds of the general formula (I)

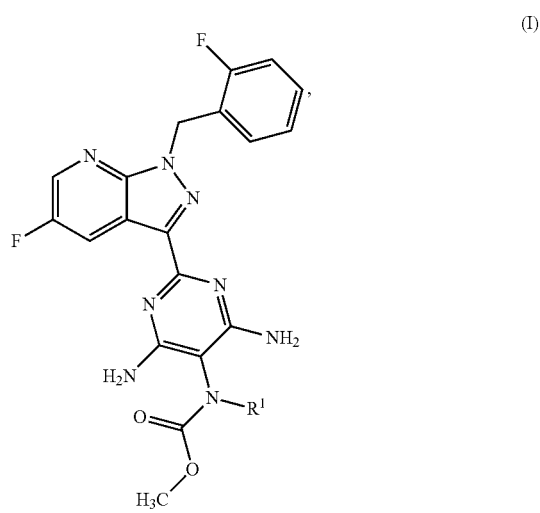

in which
R$^1$ represents hydrogen or (C$_1$-C$_4$)-alkyl,
where (C$_1$-C$_4$)-alkyl may be substituted by one or two substituents independently of one another selected from the group consisting of fluorine and trifluoromethyl,
and their N-oxides, salts, solvates, salts of the N-oxides and solvates of the N-oxides and salts.

Compounds according to the invention are the compounds of the formula (I) and the N-oxides, salts, solvates and solvates of the N-oxides and salts thereof, the compounds, encompassed by formula (I), of the formulae specified hereinafter and the N-oxides, salts, solvates and solvates of the N-oxides and salts thereof, and the compounds encompassed by formula (I) and specified hereinafter as working examples and the N-oxides, salts, solvates and solvates of the N-oxides and salts thereof, to the extent that the compounds encompassed by formula (I) and specified hereinafter are not already N-oxides, salts, solvates and solvates of the N-oxides and salts.

In the context of the present invention, preferred salts are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of the solvates in which the coordination is with water. Preferred solvates in the context of the present invention are hydrates.

Depending on their structure, the compounds according to the invention may exist in different stereoisomeric forms, i.e. in the form of configurational isomers or if appropriate also as conformational isomers (enantiomers and/or diastereomers, including those in the case of atropisomers). The present invention therefore encompasses the enantiomers or diastereomers and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention compound has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the context of the present invention, unless specified otherwise, the substituents are defined as follows:

In the context of the invention, alkyl represents a straight-chain or branched alkyl radical having 1 to 4 carbon atoms. The following may be mentioned by way of example and by way of preference: methyl, ethyl, n-propyl, isopropyl, n-butyl, isobutyl, 1-methylpropyl, tert-butyl.

In the context of the invention, halogen represents fluorine, chlorine, bromine and iodine.

If radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, preference is given to compounds of the formula (I) in which
$R^1$ represents hydrogen or methyl,
where methyl may be substituted by a trifluoromethyl substituent,
and their salts, solvates and solvates of the salts.

In the context of the present invention, particular preference is given to the following compounds of the formula (I):
methyl {4,6-diamino-2-[5-fluoro-1-(2-fluorobenzyl)-1H-pyrazolo[3,4-b]pyridin-3-yl]pyrimidin-5-yl}carbamate
methyl {4,6-diamino-2-[5-fluoro-1-(2-fluorobenzyl)-1H-pyrazolo[3,4-b]pyridin-3-yl]pyrimidin-5-yl}methylcarbamate
methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate
methyl {4,6-diamino-2-[5-fluoro-1-(2-fluorobenzyl)-1H-pyrazolo[3,4-b]pyridin-3-yl]pyrimidin-5-yl}carbamate hydrochloride
methyl {4,6-diamino-2-[5-fluoro-1-(2-fluorobenzyl)-1H-pyrazolo[3,4-b]pyridin-3-yl]pyrimidin-5-yl}carbamate sulphate
methyl {4,6-diamino-2-[5-fluoro-1-(2-fluorobenzyl)-1H-pyrazolo[3,4-b]pyridin-3-yl]pyrimidin-5-yl}carbamate phosphate
methyl {4,6-diamino-2-[5-fluoro-1-(2-fluorobenzyl)-1H-pyrazolo[3,4-b]pyridin-3-yl]pyrimidin-5-yl}carbamate mesylate
methyl {4,6-diamino-2-[5-fluoro-1-(2-fluorobenzyl)-1H-pyrazolo[3,4-b]pyridin-3-yl]pyrimidin-5-yl}carbamate ethane-1,2-disulphonate
methyl {4,6-diamino-2-[5-fluoro-1-(2-fluorobenzyl)-1H-pyrazolo[3,4-b]pyridin-3-yl]pyrimidin-5-yl}carbamate maleate
methyl {4,6-diamino-2-[5-fluoro-1-(2-fluorobenzyl)-1H-pyrazolo[3,4-b]pyridin-3-yl]pyrimidin-5-yl}carbamate nitrate The individual radical definitions specified in the respective combinations or preferred combinations of radicals are, independently of the respective combinations of the radicals specified, also replaced as desired by radical definitions of other combinations.

Particular preference is given to combinations of two or more of the preferred ranges mentioned above.

The invention further provides a process for preparing the compounds of the formula (I) according to the invention, characterized in that the compound of the formula (II)

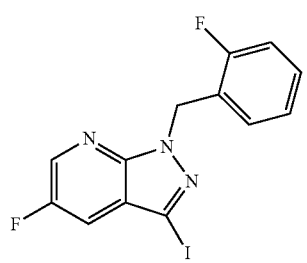
(II)

[A] is reacted in an inert solvent in the presence of hexabutyltin and a suitable palladium catalyst with intermediate formation of a tin species with the compound of the formula (III)

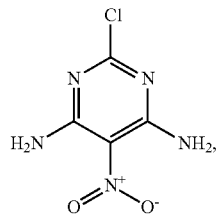
(III)

to give the compound of the formula (IV)

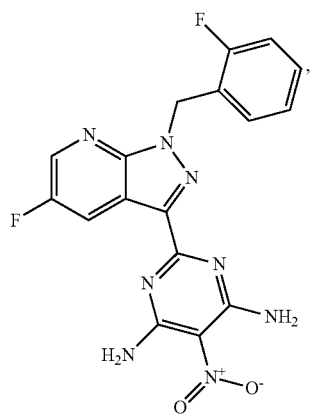
(IV)

this is then reduced in an inert solvent with a suitable reducing agent to give the compound of the formula (V)

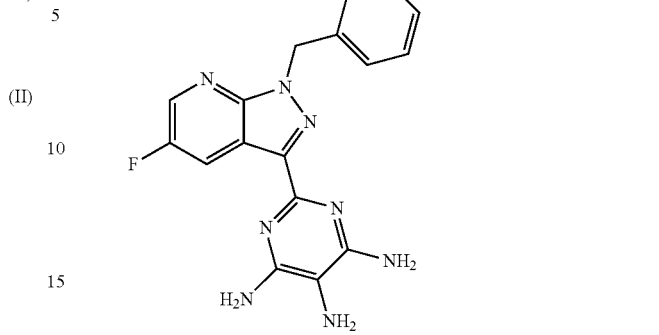
(V)

and this is then reacted in the presence of a suitable base in the presence or absence of a solvent with methyl chloroformate to give the compound of the formula (I-A)

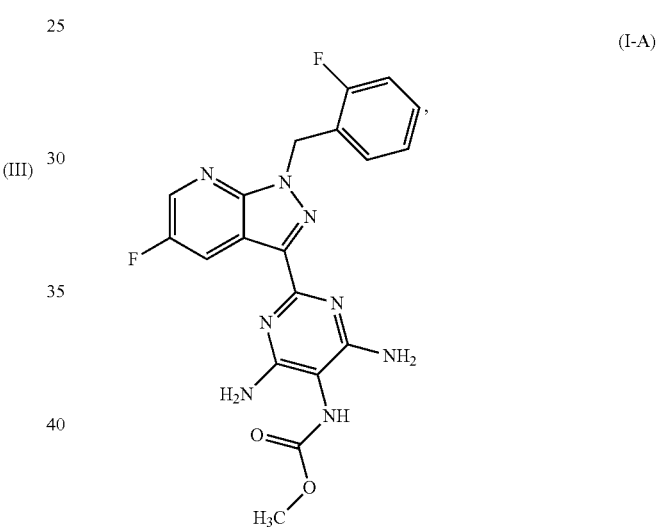
(I-A)

or

[B] the compound of the formula (II) is reacted in an inert solvent with copper cyanide to give the compound of the formula (VI)

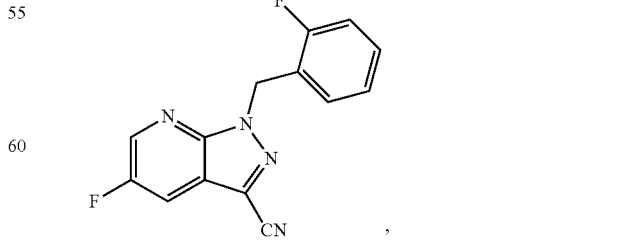
(VI)

this is then, under acidic conditions, converted into the compound of the formula (VII)

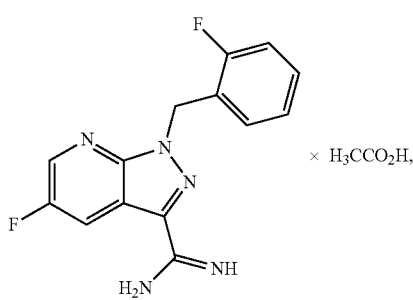

(VII) × H₃CCO₂H, this is subsequently reacted in an inert solvent in the presence of a suitable base with the compound of the formula (VIII)

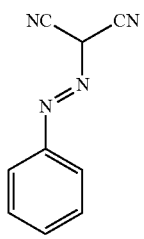

(VIII)

to give the compound of the formula (IX)

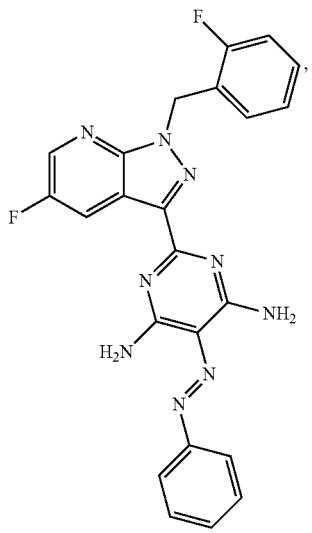

(IX)

and this is then reduced in an inert solvent in the presence of a suitable reducing agent to give the compound (V), and this is subsequently reacted further according to process [A] to give compound (I-A), or

[C] the compound of the formula (I-A) is reacted in an inert solvent in the presence of a suitable base with a compound of the formula (X)

$$R^{14}—X^1 \quad (X),$$

in which
$R^{14}$ a represents $(C_1-C_4)$-alkyl,
where $(C_1-C_4)$-alkyl may be substituted by one or two substituents independently of one another selected from the group consisting of fluorine and trifluoromethyl,
and
$X^1$ represents a leaving group such as, for example, halogen, in particular bromine or iodine, trichloromethanesulphonate, mesylate or tosylate
to give a compound of the formula (I-B)

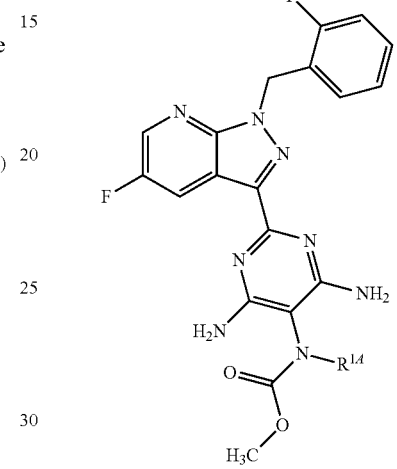

(I-B)

in which $R^{14}$ has the meaning given above,
and the resulting compounds of the formulae (I-A) and (I-B) are, where appropriate, converted with the appropriate (i) solvents and/or (ii) acids or bases into their solvates, salts and/or solvates of the salts.

Inert solvents for process step (II)+(III)→(IV) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), dimethylacetamide, N-methylpyrrolidone (NMP), pyridine, acetonitrile, sulpholane or else water. It is equally possible to use mixtures of the solvents mentioned. Preference is given to dioxane.

Suitable palladium catalysts for process step (II)+(III)→(IV) are, for example, palladium on activated carbon, palladium(II) acetate, tetrakis(triphenylphosphine)palladium(0), bis(triphenylphosphine)palladium(II) chloride, bis(acetonitrile)palladium(II) chloride and [1,1'-bis(diphenylphosphino)ferrocene]dichloropalladium(II)/dichloromethane complex, if appropriate in combination with additional phosphane ligands such as, for example, (2-biphenyl)di-tert-butylphosphine, dicyclohexyl[2',4',6'-tris(1-methylethyl)biphenyl-2-yl]phosphane (XPHOS), bis(2-phenylphosphinophenyl) ether (DPEphos) or 4,5-bis(diphenylphosphino)-9,9-dimethylxanthene (Xantphos) [cf., for example, Hassan J. et al., *Chem. Rev.* 102, 1359-1469 (2002)]. Preference is given to using tetrakis(triphenylphosphine)palladium(0).

The reaction (II)+(III)→(IV) is generally carried out in a temperature range of from +20° C. to +180° C., preferably from +50° C. to +120° C., if appropriate in a microwave. The reaction can be carried out at atmospheric, elevated or reduced pressure (for example from 0.5 to 5 bar). The reaction is generally carried out at atmospheric pressure.

The reductions (IV)→(V) and (IX)→(V) are carried out in the presence of a suitable catalyst in an inert solvent in a temperature range of from +20° C. to +40° C. under hydrogen of atmospheric pressure.

Inert solvents for the reductions (IV)→(V) and (IX)→(V) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is equally possible to use mixtures of the solvents mentioned. Preference is given to DMF and pyridine.

Suitable catalysts for the reactions (IV)→(V) and (IX)→(V) are, for example, palladium on activated carbon, platinum on carbon, palladium hydroxide or Raney nickel.

Alternatively, the reductions (IV)→(V) and (IX)→(V) can be carried out using a metal or metal salt such as, for example, iron, zinc or tin(II) chloride in a suitable acid such as, for example, hydrogen chloride/hydrochloric acid, sulphuric acid, phosphoric acid or acetic acid in a temperature range of from +20° C. to +140° C.

Inert solvents for process step (V)→(I-A) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, halogenated hydrocarbons such as dichloromethane, trichloromethane, carbon tetrachloride, trichloroethylene or chlorobenzene, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), acetonitrile or else water. It is equally possible to use mixtures of the solvents mentioned. Preference is given to dimethylformamide and toluene and also to a mixture of dimethylformamide and toluene.

Suitable bases for the process step (V)→(I-A) are alkali metal hydrides such as sodium hydride, alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to pyridine.

The reaction (V)→(I-A) is generally carried out in a temperature range of from −10° C. to +30° C., preferably from 0° C. to +20° C. The reaction can be carried out at atmospheric, elevated or reduced pressure (for example from 0.5 to 5 bar). The reaction is generally carried out at atmospheric pressure.

Inert solvents for process step (II)→(VI) are, for example, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is equally possible to use mixtures of the solvents mentioned. Preference is given to DMSO.

The reaction (II)→(VI) is generally carried out in a temperature range of from +20° C. to +180° C., preferably from +100° C. to +160° C., if appropriate in a microwave. The reaction can be carried out at atmospheric, elevated or reduced pressure (for example from 0.5 to 5 bar). The reaction is generally carried out at atmospheric pressure.

The reaction (VI)→(VII) is carried out using methods known to the person skilled in the art in a two-step process initially with formation of the imino ester using sodium methoxide in methanol at from 0° C. to +40° C. and subsequent nucleophilic addition of an ammonia equivalent such as, for example, ammonia or ammonium chloride in acetic acid with formation of the amidine (VII) at from +50 to +150° C.

Inert solvents for process step (VII)+(VIII)→(IX) are alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is equally possible to use mixtures of the solvents mentioned. Preference is given to DMF.

Suitable bases for the process step (VII)+(VIII)→(IX) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (VII)+(VIII)→(IX) is generally carried out in a temperature range of from +20° C. to +150° C., preferably from +80° C. to +120° C., if appropriate in a microwave. The reaction can be carried out at atmospheric, elevated or reduced pressure (for example from 0.5 to 5 bar). The reaction is generally carried out at atmospheric pressure.

The compound of the formula (VIII) can be prepared analogously to the literature L. F. Cavalieri, J. F. Tanker, A. Bendich, J. Am. Chem. Soc., 1949, 71, 533.

Inert solvents for the reaction (I-A)→(I-B) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine or acetonitrile. Preference is given to tetrahydrofuran.

Suitable bases for the process step (I-A)→(I-B) are alkali metal hydrides such as potassium hydride or sodium hydride, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, amides such as sodium amide, lithium bis(trimethylsilyl)amide, sodium bis(trimethylsilyl)amide or potassium bis(trimethylsilyl)amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to lithium bis(trimethylsilyl)amide, sodium bis(trimethylsilyl)amide and sodium hydride.

The reaction (I-A)→(I-B) is generally carried out in a temperature range of from −78° C. to +40° C., preferably from 0° C. to +20° C. The reaction can be carried out at atmospheric, elevated or reduced pressure (for example from 0.5 to 5 bar). The reaction is generally carried out at atmospheric pressure.

The preparation processes described can be illustrated in an exemplary manner by the synthesis schemes below (Schemes 1 to 3):

-continued

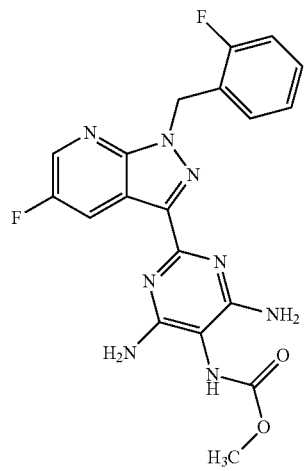

[a): Pd(PPh₃)₄, hexabutylditin; b) H₂, Pd—C; c) methyl chloroformate, pyridine].

Scheme 1

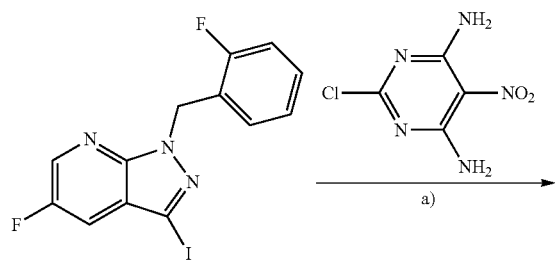

Scheme 2

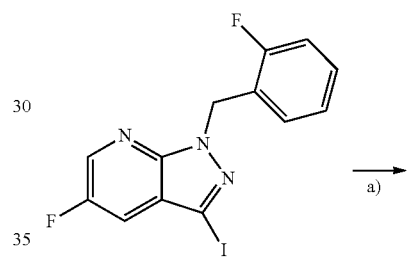

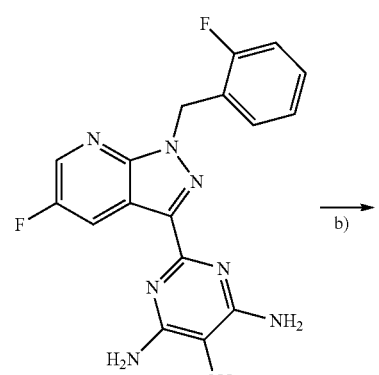

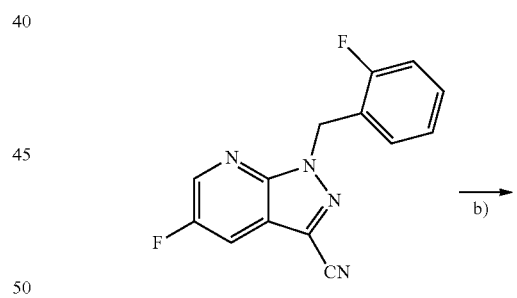

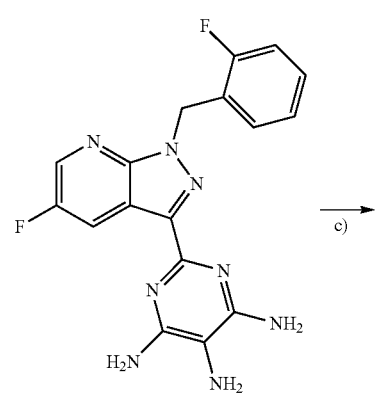

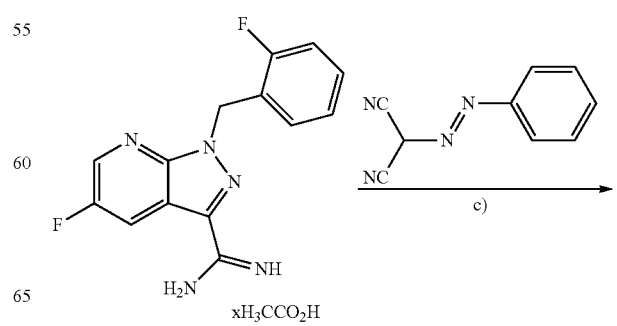

-continued

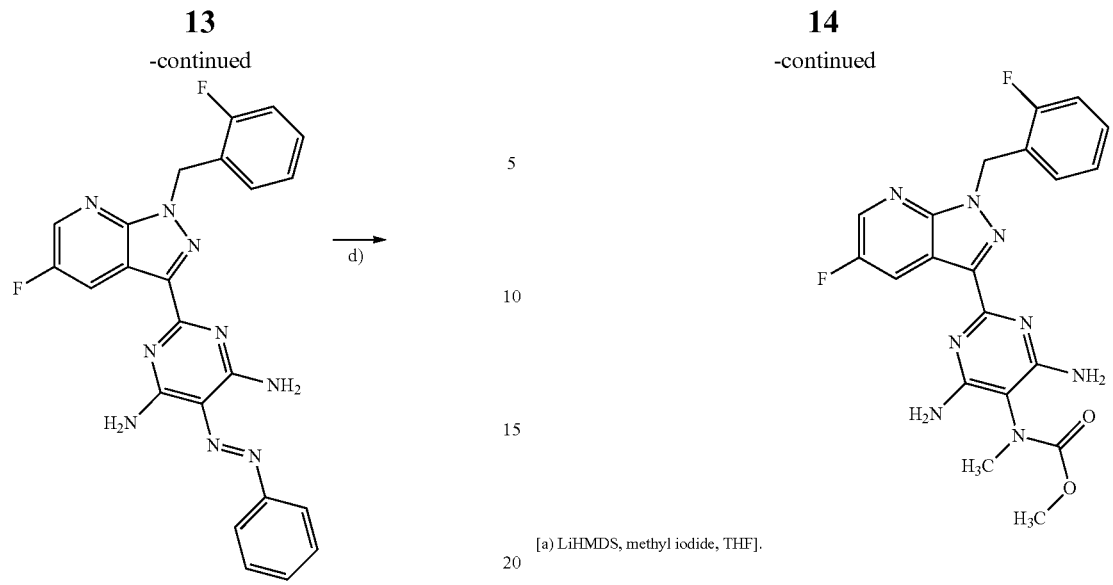

[a) LiHMDS, methyl iodide, THF].

The compound of the formula (II) can be prepared by cyclizing the compound of the formula (X)

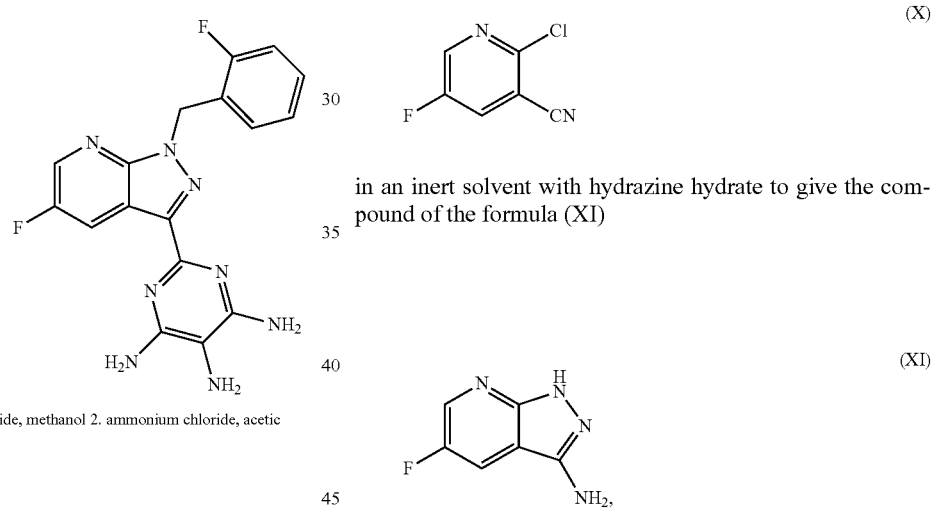

in an inert solvent with hydrazine hydrate to give the compound of the formula (XI)

(XI)

then reacting this compound in an inert solvent in the presence of a suitable Lewis acid initially with isopentyl nitrite to give the corresponding diazonium salt and then converting this salt directly with sodium iodide into the compound of the formula (XII)

(XII)

and then reacting this compound in an inert solvent in the presence of a suitable base with the compound of the formula (XIII)

[a]: CuCN, DMSO; b): 1. sodium methoxide, methanol 2. ammonium chloride, acetic acid; c): triethylamine d): H₂,Pd—C].

Scheme 3

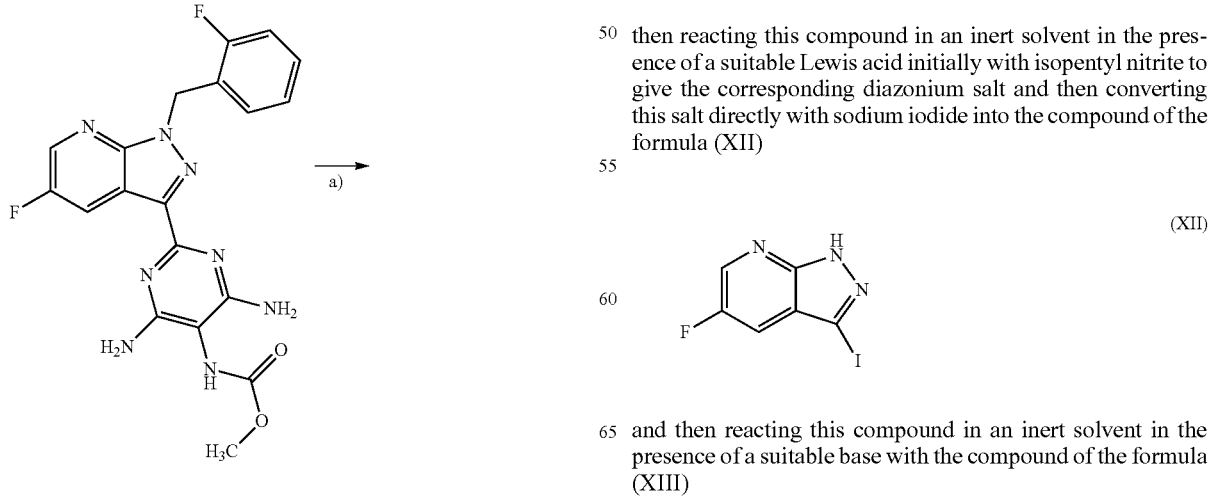

(XIII)

Inert solvents for process step (X)→(XI) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is equally possible to use mixtures of the solvents mentioned. 1,2-Ethanediol is preferred.

The reaction (X)→(XI) is generally carried out in a temperature range of from +60° C. to +200° C., preferably from +120° C. to +180° C. The reaction can be carried out at atmospheric, elevated or reduced pressure (for example from 0.5 to 5 bar). The reaction is generally carried out at atmospheric pressure.

Inert solvents for the reaction (XI)→(XII) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine or acetonitrile. Preference is given to DMF.

Suitable Lewis acids for the process step (XI)→(XII) are boron trifluoride/diethyl ether complex, cerium(IV) ammonium nitrate (CAN), tin(II) chloride, lithium perchlorate, zinc (II) chloride, indium(III) chloride or indium(III) bromide. Preference is given to boron trifluoride/diethyl ether complex.

The reaction (XI)→(XII) is generally carried out in a temperature range of from −78° C. to +40° C., preferably from 0° C. to +20° C. The reaction can be carried out at atmospheric, elevated or reduced pressure (for example from 0.5 to 5 bar). The reaction is generally carried out at atmospheric pressure.

Inert solvents for the reaction (XII)+(XIII)→(II) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine or acetonitrile. Preference is given to DMF.

Suitable bases for the process step (XII)+(XIII)→(II) are alkali metal hydrides such as potassium hydride or sodium hydride, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide, sodium tert-butoxide, amides such as sodium amide, lithium bis(trimethylsilyl)amide, sodium bis(trimethylsilyl)amide or potassium bis(trimethylsilyl) amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to caesium carbonate.

The reaction (XII)+(XIII)→(II) is generally carried out in a temperature range of from 0° C. to +60° C., preferably from +10° C. to +25° C. The reaction can be carried out at atmospheric, elevated or reduced pressure (for example from 0.5 to 5 bar). The reaction is generally carried out at atmospheric pressure.

The preparation process described can be illustrated in an exemplary manner by the synthesis scheme below (Scheme 4):

Scheme 4

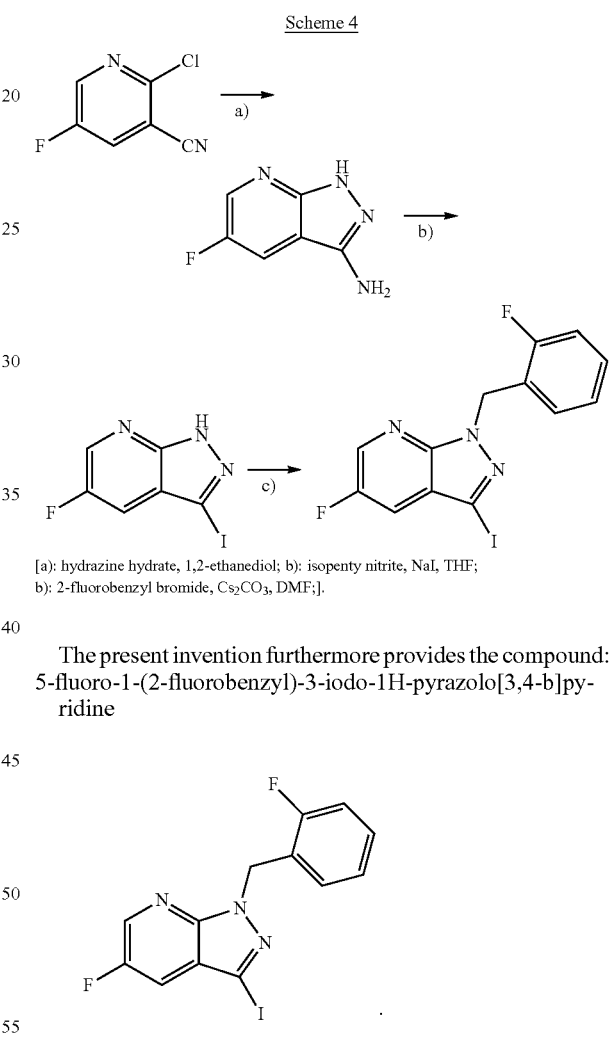

[a]: hydrazine hydrate, 1,2-ethanediol; b): isopentyl nitrite, NaI, THF;
b): 2-fluorobenzyl bromide, Cs₂CO₃, DMF;].

The present invention furthermore provides the compound: 5-fluoro-1-(2-fluorobenzyl)-3-iodo-1H-pyrazolo[3,4-b]pyridine

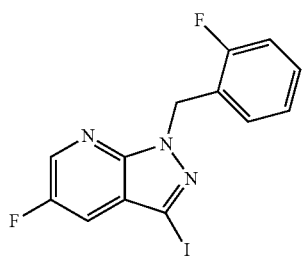

The present invention furthermore provides the compound: 5-fluoro-3-iodo-1H-pyrazolo[3,4-b]pyridine

The compounds of the formulae (III) and (XIII) are commercially available, known from the literature or can be prepared in analogy to literature processes.

The compound of the formula (X) is known from the literature [cf., for example, Winn M., *J. Med. Chem.* 1993, 36, 2676-7688; EP 634 413-A1; CN 1613849-A; EP 1626045-A1; WO 2009/018415] and can be prepared in analogy to literature processses or as shown in the synthesis scheme below (Scheme 5):

Scheme 5

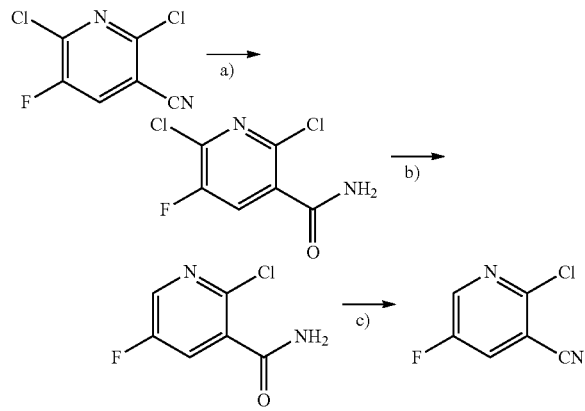

[a]: sulphuric acid, b): zinc, methanol, glacial acetic acid; c): trifluoroacetic anhydride, dichloromethane].

The compounds according to the invention act as stimulators of soluble guanylate cyclase and have an identical or improved therapeutic profile compared to compounds known from the prior art, such as, for example, with respect to their in vivo properties such as, for example, their pharmacokinetic and pharmacodynamic behaviour and/or their dose-activity relationship and/or their safety profile. They are therefore suitable for the treatment and/or prophylaxis of diseases in man and animals.

The compounds according to the invention lead to vasorelaxation, to an inhibition of platelet aggregation and to a reduction in blood pressure, and also to an increase in coronary blood flow. These effects are mediated via direct stimulation of soluble guanylate cyclase and intracellular cGMP increase. Moreover, the compounds according to the invention enhance the effect of substances increasing the cGMP concentration, such as, for example, EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term heart failure also includes more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

In addition, the compounds according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemias, sitosterolaemia, xanthomatosis, Tangier disease, adipositas, obesity and of combined hyperlipidaemias and metabolic syndrome.

The compounds according to the invention can additionally be used for the treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds according to the invention are furthermore suitable for the treatment and/or prophylaxis of kidney disorders, in particular of acute and chronic renal insufficiency and acute and chronic renal failure. In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminurea, macroalbuminurea, laesions on glomerulae and arterioles, tubular dilatation, hyperphosphataemia and/or need for dialysis. The present invention also comprises the use of the compounds according to the invention for the treatment and/or prophylaxis of sequelae of renal insufficiency, for example pulmonary oedema, heart failure, uraemia, anaemia, electrolyte disturbances (for example hypercalaemia, hyponatraemia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarkoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention also represent active compounds for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of sequelae of cerebral infarct (Apoplexia cerebri) such as stroke, cerebral ischaemias and skull-brain trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitreoretinopathy and disorders of the connective tissue (for example sarcoidosis).

The compounds according to the invention are furthermore suitable for controlling postoperative scarring, for example as a result of glaucoma operations.

The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides the use of the compounds according to the invention for the treatment and/or prophylaxis of heart failure, angina pectoris, hypertension, pulmonary hypertension, ischaemias, vascular disorders, kidney failure, thromboembolic disorders, fibrotic disorders and arteriosclerosis.

The present invention further provides the compounds according to the invention for use in a method for the treatment and/or prophylaxis of heart failure, angina pectoris, hypertension, pulmonary hypertension, ischaemias, vascular disorders, kidney failure, thromboembolic disorders, fibrotic disorders and arteriosclerosis.

The present invention further provides for the use of the compounds according to the invention for producing a medicament for treatment and/or prophylaxis of disorders, in particular the disorders mentioned above.

The present invention further provides for the use of the compounds according to the invention for producing a medicament for treatment and/or prophylaxis of heart failure, angina pectoris, hypertension, pulmonary hypertension, ischaemias, vascular disorders, kidney failure, thromboembolic disorders, fibrotic disorders and arteriosclerosis.

The present invention further provides a method for treatment and/or prophylaxis of disorders, in particular the disorders mentioned above, using an effective amount of at least one of the compounds according to the invention.

The present invention further provides a method for treatment and/or prophylaxis of heart failure, angina pectoris, hypertension, pulmonary hypertension, ischaemias, vascular disorders, kidney failure, thromboembolic disorders, fibrotic disorders and arteriosclerosis using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;

agents having an antithrombotic effect, for example and with preference from the group of platelet aggregation inhibitors, of anticoagulants or of profibrinolytic substances;

active compounds which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or active compounds which alter lipid metabolism, for example and with preference from the group of thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists;

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, by way of example and preferably, aspirin, clopidogrel, ticlopidin or dipyridamol.

In a preferred embodiment of the invention, the compounds according to the invention are administered in combination with a thrombin inhibitor such as, by way of example and preferably, ximelagatran, dabigatran, melagatran, bivalirudin or clexane.

In a preferred embodiment of the invention, the compounds according to the invention are administered in combination with a GPIIb/IIIa antagonist such as, by way of example and preferably, tirofiban or abciximab.

In a preferred embodiment of the invention, the compounds according to the invention are administered in combination with a factor Xa inhibitor such as, by way of example and preferably, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist such as, by way of example and preferably, coumarin.

Agents which lower blood pressure are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist such as, by way of example and preferably, nifedipine, amlodipine, verapamil or diltiazem.

In a preferred embodiment of the invention, the compounds according to the invention are administered in combination with an alpha-1 receptor blocker such as, by way of example and preferably, prazosin.

In a preferred embodiment of the invention, the compounds according to the invention are administered in combination with a beta receptor blocker such as, by way of example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, by way of example and preferably, losartan, candesartan, valsartan, telmisartan or embusartan.

In a preferred embodiment of the invention, the compounds according to the invention are administered in combination with an ACE inhibitor such as, by way of example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, by way of example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a loop diuretic such as, for example, furosemide, torasemide, bumetanide and piretanide, with potassium-sparing diuretics such as, for example, amiloride and triamterene, with aldosterone antagonists such as, for example, spironolactone, potassium canrenoate and eplerenone and also thiazide diuretics such as, for example, hydrochlorothiazide, chlorthalidone, xipamide and indapamide.

Active compounds which alter lipid metabolism are preferably understood to mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists;

In a preferred embodiment of the invention, the compounds according to the invention are administered in combination with a CETP inhibitor such as, by way of example and preferably, dalcetrapib, BAY 60-5521, anacetrapib or CETP vaccine (CETi-1).

In a preferred embodiment of the invention, the compounds according to the invention are administered in combination with a thyroid receptor angonist such as, by way of example and preferably, D-thyroxin, 3,5,3'-triiodothyronin (T3), CGS 23425 or axitirome (CGS 26214).

In a preferred embodiment of the invention, the compounds according to the invention are administered in combination with a HMG-CoA reductase inhibitor from the class of the statins such as, by way of example and preferably, lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor such as, by way of example and preferably, BMS-188494 or TAK-475.

In a preferred embodiment of the invention, the compounds according to the invention are administered in combination with an ACAT inhibitor such as, by way of example and preferably, avasimibe, melinamide, pactimibe, eflucimibe or SMP-797.

In a preferred embodiment of the invention, the compounds according to the invention are administered in combination with an MTP inhibitor such as, by way of example and preferably, implitapide, BMS-201038, R-103757 or JTT-130.

In a preferred embodiment of the invention, the compounds according to the invention are administered in combination with a PPAR-gamma angonist such as, by way of example and preferably, pioglitazone or rosiglitazone.

In a preferred embodiment of the invention, the compounds according to the invention are administered in combination with a PPAR-delta angonist such as, for example and preferably, GW 501516 or BAY 68-5042.

In a preferred embodiment of the invention, the compounds according to the invention are administered in combination with a cholesterol absorption inhibitor such as, by way of example and preferably, ezetimibe, tiqueside or pamaqueside.

In a preferred embodiment of the invention, the compounds according to the invention are administered in combination with a lipase inhibitor, a preferred example being orlistat.

In a preferred embodiment of the invention, the compounds according to the invention are administered in combination with a polymeric bile acid adsorbent such as, by way of example and preferably, cholestyramine, colestipol, colesolvam, CholestaGel or colestimide.

In a preferred embodiment of the invention, the compounds according to the invention are administered in combination with a bile acid reabsorption inhibitor such as, by way of example and preferably, ASBT (=IBAT) inhibitors, for example AZD-7806, S-8921, AK-105, BARI-1741, SC-435 or SC-635

In a preferred embodiment of the invention, the compounds according to the invention are administered in combination with an lipoprotein(a) antagonist such as, by way of example and preferably, gemcabene calcium (CI-1027) or nicotinic acid.

The present invention further provides medicaments which comprise at least one compound according to the invention, typically together with one or more inert, nontoxic, pharmaceutically suitable auxiliaries, and the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/wafers which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/wafers or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral or parenteral administration is preferred, especially oral administration.

The compounds according to the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of relatively large amounts, it may be advisable to divide these into several individual doses over the course of the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration data for liquid/liquid solutions are based in each case on volume.

A. EXAMPLES

Abbreviations and Acronyms aq. aqueous solution
calc. calculated
br s broad singlet (in NMR)
DCI direct chemical ionization (in MS)
dec. decomposition point
DMF dimethylformamide
DMSO dimethyl sulphoxide
DSC dynamic differential calorimetry
eq. equivalent(s)
ESI electrospray ionization (in MS)
Et ethyl
fnd. found
h hour(s)
HPLC high-pressure high-performance liquid chromatography
HRMS high-resolution mass spectrometry
conc. concentrated
LC-MS liquid chromatography-coupled mass spectrometry
LiHMDS lithium hexamethyldisilazide
Me methyl
min minute(s)
MS mass spectrometry
NMR nuclear magnetic resonance spectrometry
$Pd_2dba_3$ tris(dibenzylideneacetone)dipalladium
Ph phenyl
PLM polarized light microscope
RT room temperature
$R_t$ retention time (in HPLC)
TGA thermogravimetric analysis
THF tetrahydrofuran
UV ultraviolet spectrometry
v/v volume to volume ratio (of a solution)

LC/MS Methods:

Method 1: MS instrument type: Waters ZQ; apparatus type HPLC: Agilent 1100 Series; UV DAD; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.

Method 2: Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 5° C.; flow rate: 0.40 ml/min; UV detection: 210-400 nm.

Method 3: Instrument: Micromass Quattro Premier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+ 0.5 ml of 50% strength formic acid; gradient: 0.0 min 90% A 0.1 min 90% A 1.5 min 10% A 2.2 min 10% A; oven 50° C.; flow rate: 0.33 ml/min; UV detection: 210 nm.

General Methods:

PLM: The polarized light microscopy was carried out using a Clemex PS3 polarized light microscope particle size system with a Leica DM microscope proceeded with 50×, 100×, 200×, and 500× lenses, a high-resolution monochrome 1600×1200 pixel digital camera and a motorized X-Y Marzhauser station (controlled by a Clemex ST-2000 controller). The samples of the crystalline material were measured on a glass slide (76×26 mm) in a drop of oil, the sample being covered with a cover glass (22×40 mm)

DSC: The melting points were determined by dynamic differential calorimetry. The determination was carried out using a Mettler-Toledo 823$^e$ DSC instrument provided with a TSO801RO sample robot and STAR$^e$ software. About 1.5 to 3 mg of the sample were weighed out into a small aluminium pan, which was then closed with a perforated cap. The heat flow was measured in a temperature range of from 30 to 400° C. at a heating rate of 10° C./min and under an argon stream of 30 ml/min.

TGA: The thermogravimetric analysis was carried out using a Mettler-Toledo TGA/SDTA851$^e$ TGA instrument provided with a TSO801RO sample robot and STARe software. About 1.5 to 3 mg of the sample were weighed out into a small open aluminium pan (100 μl). The sample weight was measured in a temperature range of from 30 to 400° C. at a heating rate of 10° C./min and under an argon stream of 30 ml/min.

The elemental analyses were carried out by Currenta GmbH & Co. using methods known to the person skilled in the art, in accordance with industry norm DIN-ISO 17025.

Starting Materials and Intermediates:

Example 1A 2,6-Dichloro-5-fluoronicotinamide

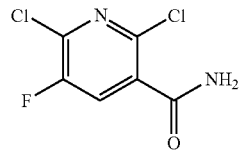 [SMILES: NC(=O)c1cc(F)c(Cl)nc1Cl]

A suspension of 25 g (130.90 mmol) of 2,6-dichloro-5-fluoro-3-cyanopyridine in conc. sulphuric acid (125 ml) was stirred at 60-65° C. for 1 h. After cooling to RT, the contents of the flask were poured into ice-water and extracted three times with ethyl acetate (100 ml each time). The combined organic phases were washed with water (100 ml) and then with saturated aqueous sodium hydrogen carbonate solution (100 ml), dried and concentrated on a rotary evaporator. The material obtained was dried under high vacuum.

Yield: 24.5 g (90% of theory)

$^1$H NMR (400 MHz, DMSO-d$_6$): δ=7.95 (br s, 1H), 8.11 (br s, 1H), 8.24 (d, 1H).

Example 2A

2-Chloro-5-fluoronicotinamide

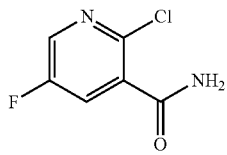 [SMILES: NC(=O)c1cc(F)cnc1Cl]

At RT, 44 g (210.58 mmol) of 2,6-dichloro-5-fluoronicotinamide were added to a suspension of 21.9 g (335.35 mmol) of zinc in methanol (207 ml). Acetic acid (18.5 ml) was then added, and the mixture was heated with stirring at reflux for 24 h. The contents of the flask were then decanted from the zinc, and ethyl acetate (414 ml) and saturated aqueous sodium hydrogen carbonate solution (414 ml) were added, followed by intense extractive stirring. Subsequently the reaction mixture was filtered with suction through kieselguhr and the filter product was washed three times with ethyl acetate (517 ml each time). The organic phase was separated off and the aqueous phase was washed with ethyl acetate (258 ml). The combined organic phases were washed once with saturated aqueous sodium hydrogen carbonate solution (414 ml), dried and concentrated under reduced pressure. Dichloromethane (388 ml) was added to the crystals obtained in this manner, and the mixture was stirred for 20 min. The mixture was once more filtered off with suction, washed with diethyl ether and sucked dry.

Yield: 20.2 g (53% of theory)

$^1$H NMR (400 MHz, DMSO-d$_6$): δ=7.87 (br s, 1H), 7.99 (dd, 1H), 8.10 (br s, 1H), 8.52 (d, 1H).

Example 3A

2-Chloro-5-fluoronicotinonitrile

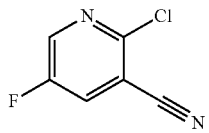

81.2 ml (582.25 mmol) of triethylamine were added to a suspension of 46.2 g (264.66 mmol) of 2-chloro-5-fluoronicotinamide in dichloromethane (783 ml), and the mixture was cooled to 0° C. Then, with stirring, 41.12 ml (291.13 mmol) of trifluoroacetic anhydride were added slowly dropwise and the mixture was stirred at 0° C. for 1.5 h. The reaction solution was subsequently washed twice with saturated aqueous sodium bicarbonate solution (391 ml each time), dried and concentrated under reduced pressure.

Yield: 42.1 g (90% of theory)

$^1$H NMR (400 MHz, DMSO-d$_6$): δ=8.66 (dd, 1H), 8.82 (d, 1H).

Example 4A

5-Fluoro-1H-pyrazolo[3,4-b]pyridine-3-amine

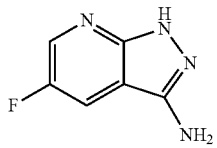

A suspension of 38.5 g (245.93 mmol) of 2-chloro-5-fluoronicotinonitrile was initially charged in 1,2-ethanediol (380 ml), and hydrazine hydrate (119.6 ml, 2.459 mol) was then added. The mixture was heated under reflux with stirring for 4 h. The product precipitated on cooling. Water (380 ml) was added to the yellow crystals, and the mixture was subjected to extractive stirring at RT for 10 min. The suspension was then filtered with suction over a frit, and the filter product was washed with water (200 ml) and with −10° C. cold THF (200 ml). The residue was dried under high vacuum over phosphorus pentoxide.

Yield: 22.8 g (61% of theory)

$^1$H NMR (400 MHz, DMSO-d$_6$): δ=5.54 (s, 2H), 7.96 (dd, 1H), 8.38 (m, 1H), 12.07 (m, 1H).

Example 5A

5-Fluoro-3-iodo-1H-pyrazolo[3,4-b]pyridine

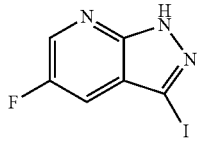 [SMILES: Fc1cnc2[nH]nc(I)c2c1]

10 g (65.75 mmol) of 5-fluoro-1H-pyrazolo[3,4-b]pyridine-3-amine were initially charged in THF (329 ml), and the mixture was cooled to 0° C. 16.65 ml (131.46 mmol) of boron trifluoride diethyl ether complex were then added slowly. The reaction mixture was cooled further to −10° C. A solution of 10.01 g (85.45 mmol) of isopentyl nitrite in THF (24.39 ml) was then added slowly, and the mixture was stirred for a further 30 min. The mixture was diluted with cold diethyl ether (329 ml) and the resulting solid was isolated by filtration. A little at a time, the diazonium salt thus prepared was added to a cold (0° C.) solution of 12.81 g (85.45 mmol) of sodium iodide in acetone (329 ml), and the mixture was stirred at RT for 30 min. The reaction mixture was poured into ice-water (1.8 l) and extracted twice with ethyl acetate (487 ml each time). The collected organic phases were washed with saturated aqueous sodium chloride solution (244 ml), dried, filtered and concentrated. This gave 12.1 g (86% purity, 60% of theory) of the desired compound in the form of a brown solid. The crude product was reacted without further purification.

LC-MS (method 1): $R_t$=1.68 min; MS (ESIpos): m/z=264 (M+H)$^+$.

Example 6A

5-Fluoro-1-(2-fluorobenzyl)-3-iodo-1H-pyrazolo[3,4-b]pyridine

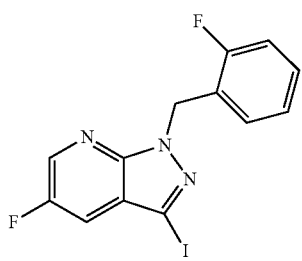 [SMILES: Fc1cnc2c(c1)c(I)nn2Cc1ccccc1F]

141 g (462.11 mmol) of the compound from Example 5A were introduced into DMF (2538 ml), and 96.09 g (508.32 mmol) of 2-fluorobenzyl bromide and 165.62 g (508.32 mmol) of caesium carbonate were then added. The mixture was stirred at RT for two hours. The reaction mixture was then poured into saturated aqueous sodium chloride solution (13 670 ml) and extracted twice with ethyl acetate (5858 ml). The collected organic phases were washed with saturated aqueous sodium chloride solution (3905 ml), dried, filtered and concentrated. The residue was chromatographed on silica gel (mobile phase: petroleum ether/ethyl acetate 97:3) and the product fractions were concentrated. The resulting solid was dissolved in dichloromethane and washed once with saturated aqueous sodium thiosulphate solution (500 ml) and then with saturated aqueous sodium chloride solution (500 ml). The product was concentrated to dryness and the residue was suspended in diethyl ether, isolated by filtration with suction and dried under high vacuum. This gave 106.6 g (62% of theory) of the desired compound.

$^1$H NMR (400 MHz, DMSO-$d_6$): δ=5.73 (s, 2H), 7.13-7.26 (m, 3H), 7.33-7.41 (m, 1H), 7.94 (dd, 1H), 8.69-8.73 (m, 1H).

Example 7A

2-[5-Fluoro-1-(2-fluorobenzyl)-1H-pyrazolo[3,4-b]pyridin-3-yl]-5-nitropyrimidine-4,6-diamine

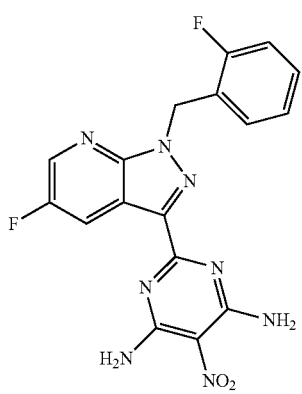 [SMILES: Nc1nc(-c2nn(Cc3ccccc3F)c3ncc(F)cc23)nc(N)c1[N+](=O)[O-]]

Under argon, 860 mg (2.32 mmol) of the compound from Example 6A were introduced into 1,4-dioxane (86 ml), and the reaction mixture was flushed with argon for 10 min. Then 3.51 ml (6.95 mmol) of hexabutylditin and 483 mg (2.55 mmol) of 2-chloro-5-nitropyrimidine-4,6-diamine (prepared by the method of *Helvetica Chimica Acta* (1951), 34, 835-40) were added. Subsequently 860 mg (0.744 mmol) of tetrakis(triphenylphosphine)palladium(0) were added and the reaction mixture was heated at reflux overnight. The mixture was then cooled to RT, water was added and the mixture was extracted twice with ethyl acetate. The collected organic phases were dried over sodium sulphate, filtered and concentrated. The residue was subjected to extractive stirring in ethyl acetate, and the solid was isolated by filtration and dried under high vacuum. This gave 355 mg (62% purity, 24% of theory) of the desired compound. The crude product was reacted without further purification.

LC-MS (method 2): $R_t$=1.03 min

MS (ESIpos): m/z=399 (M+H)$^+$

Example 8A

5-Fluoro-1-(2-fluorobenzyl)-1H-pyrazolo[3,4-b]pyridine-3-carbonitrile

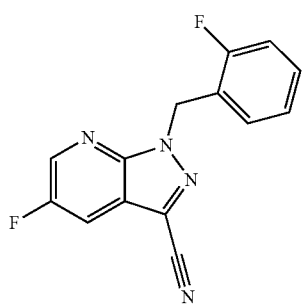 [SMILES: N#Cc1nn(Cc2ccccc2F)c2ncc(F)cc12]

A suspension of 16.03 g (43.19 mmol) of 5-fluoro-1-(2-fluorobenzyl)-3-iodo-1H-pyrazolo[3,4-b]pyridine (Example 6A) and 4.25 g (47.51 mmol) of copper cyanide was initially charged in DMSO (120 ml) and stirred at 150° C. for 2 h. After cooling, the contents of the flask were cooled to about 40° C. and poured into a solution of conc. aqueous ammonia (90 ml) and water (500 ml), ethyl acetate (200 ml) was added and the mixture was subjected to brief extractive stirring. The aqueous phase was separated off and extracted two more times with ethyl acetate (200 ml each time). The combined organic phases were washed twice with 10% strength aqueous sodium chloride solution (100 ml each time), dried and concentrated under reduced pressure. The crude product was reacted without further purification.

Yield: 11.1 g (91% of theory)

$^1$H NMR (400 MHz, DMSO-$d_6$): δ=5.87 (s, 2H), 7.17-7.42 (m, 4H), 8.52 (dd, 1H), 8.87 (dd, 1H).

Example 9A

5-Fluoro-1-(2-fluorobenzyl)-1H-pyrazolo[3,4-b]pyridine-3-carboximidamide acetate

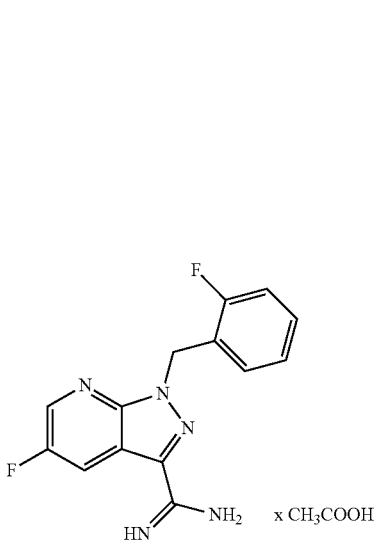 [SMILES: N=C(N)c1nn(Cc2ccccc2F)c2ncc(F)cc12]

11.1 g (41.07 mmol) of 5-fluoro-1-(2-fluorobenzyl)-1H-pyrazolo[3,4-b]pyridine-3-carbonitrile (Example 8A) were added to 2.22 g (41.07 mmol) of sodium methoxide in methanol (270 ml), and the mixture was stirred at RT for 2 h. 2.64 g (49.29 mmol) of ammonium chloride and acetic acid (9.17 ml) were then added, and the mixture was heated at reflux overnight. The mixture was then concentrated to dryness and the residue was taken up in water (100 ml) and ethyl acetate (100 ml) and adjusted to a pH of 10 using 2N aqueous sodium hydroxide solution. The mixture was stirred intensively at RT for about 1 h. The resulting suspension was filtered with suction and the filter product was washed with ethyl acetate (100 ml), with water (100 ml) and once more with ethyl acetate (100 ml). The residue was dried under high vacuum over phosphorus pentoxide.

Yield: 9.6 g (78% of theory)

MS (ESIpos): m/z=288 (M+H)$^+$ $^1$H NMR (400 MHz, DMSO-d$_6$): δ=1.85 (s, 3H), 5.80 (s, 2H), 7.14-7.25 (m, 3H), 7.36 (m, 1H), 8.42 (dd, 1H), 8.72 (dd, 1H).

Example 10A

2-[5-Fluoro-1-(2-fluorobenzyl)-1H-pyrazolo[3,4-b]pyridin-3-yl]-5-[(E)-phenyldiazenyl]pyrimidine-4,6-diamine

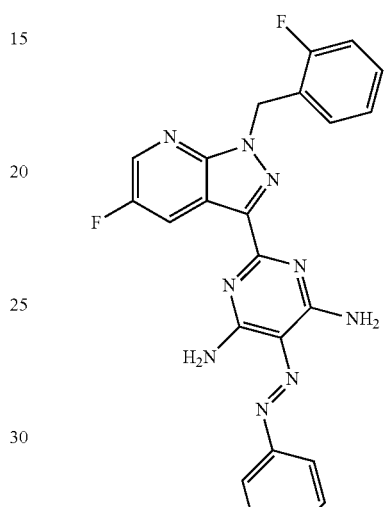

With stirring, 3.85 g (41.34 mmol) of aniline were added to water (40 ml) and conc. hydrochloric acid (7.07 ml), and this mixture was cooled to 0° C. A solution of 2.85 g (41.34 mmol) of sodium nitrite in water (21 ml) was then added dropwise at between 0° C. and 5° C., followed by stirring at 0° C. for 15 min. Thereafter, at 0° C., a solution of 4.28 g (52.25 mmol) of sodium acetate in water (19 ml) was added rapidly dropwise, and then, with thorough stirring, a solution of 2.73 g (41.34 mmol) of malononitrile in ethanol (10 ml) was added dropwise. After 2 h at 0° C., the resulting precipitate was isolated by filtration with suction and washed three times with water (50 ml each time) and with petroleum ether (50 ml). The residue, still moist, was dissolved in DMF (46 ml) and added dropwise at precisely 85° C. to a solution of 9.5 g (33.07 mmol) of 5-fluoro-1-(2-fluorobenzyl)-1H-pyrazolo[3,4-b]pyridine-3-carboximidamide acetate (Example 9A) in DMF (46 ml) and triethylamine (5.76 ml). The mixture was then stirred at 100° C. for 4 h and left to cool to RT overnight. The mixture was poured into water (480 ml) and subjected to extractive stirring at RT for 1 h. After the precipitate had been isolated by filtration with suction, it was washed twice with water (100 ml each time) and twice with methanol (50 ml each time) and then dried under a high vacuum.

Yield: 9.6 g (59% of theory)

LC-MS (method 2): R$_t$=1.21 min

MS (ESIpos): m/z=458 (M+H)$^+$

Example 11A

2-[5-Fluoro-1-(2-fluorobenzyl)-1H-pyrazolo[3,4-b]pyridin-3-yl]pyrimidine-4,5,6-triamine

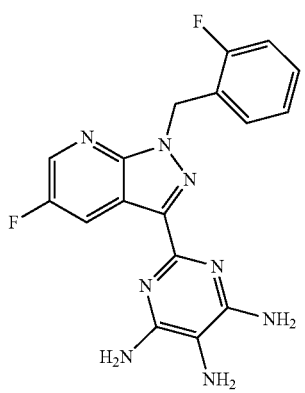 [SMILES: Nc1nc(-c2nn(Cc3ccccc3F)c3ncc(F)cc23)nc(N)c1N]

Variant A: Preparation Starting from Example 7A:

In pyridine (30 ml), 378 mg (0.949 mmol) of the compound from Example 7A were introduced and then 143 mg (0.135 mmol) of palladium (10% on carbon) were added. The mixture was hydrogenated overnight at RT under standard hydrogen pressure. The suspension was then filtered through kieselguhr and the filtercake was washed with ethanol. The filtrate was concentrated and yielded 233 mg (81% purity, 51% of theory) of the desired compound, which was reacted without further purification.

Variant B: Preparation Starting from Example 10A:

In DMF (800 ml), 39.23 g (85.75 mmol) of the compound from Example 10A were introduced and then 4 g of palladium (10% on carbon) were added. The mixture was hydrogenated with stirring overnight under standard hydrogen pressure. The batch was filtered over kieselguhr and the filter product was washed with a little DMF and then with a little methanol, and concentrated to dryness. The residue was admixed with ethyl acetate and stirred vigorously, and the precipitate was filtered off with suction, washed with ethyl acetate and diisopropyl ether and dried under a high vacuum over Sicapent.

Yield: 31.7 g (100% of theory)

LC-MS (method 2): $R_t$=0.78 min

MS (ESIpos): m/z=369 (M+H)$^+$

Working Examples

Example 1

Methyl {4,6-diamino-2-[5-fluoro-1-(2-fluorobenzyl)-1H-pyrazolo[3,4-b]pyridin-3-yl]pyrimidin-5-yl}carbamate

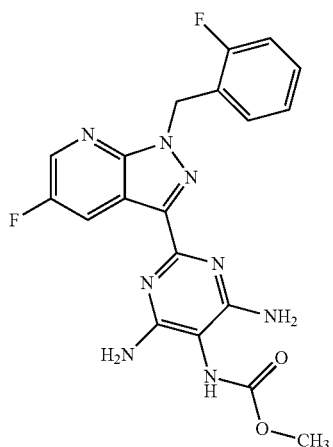

In pyridine (600 ml), 31.75 g (86.20 mmol) of the compound from Example 11A were introduced under argon and cooled to 0° C. Then a solution of 6.66 ml (86.20 mmol) of methyl chloroformate in dichloromethane (10 ml) was added dropwise and the mixture was stirred at 0° C. for 1 h. Thereafter the reaction mixture was brought to RT, concentrated under reduced pressure and co-distilled repeatedly with toluene. The residue was stirred with water/ethanol and then filtered off on a frit, after which it was washed with ethanol and ethyl acetate. Subsequently the residue was again stirred with diethyl ether, isolated by filtration with suction and then dried under a high vacuum.

Yield: 24.24 g (65% of theory)

LC-MS (method 2): $R_t$=0.79 min

MS (ESIpos): m/z=427 (M+H)$^+$ $^1$H NMR (400 MHz, DMSO-d$_6$): δ=3.62 (br. s, 3H), 5.79 (s, 2H), 6.22 (br. s, 4H), 7.10-7.19 (m, 2H), 7.19-7.26 (m, 1H), 7.32-7.40 (m, 1H), 7.67 and 7.99 (2 br. s, 1H), 8.66 (m, 1H), 8.89 (dd, 1H).

Example 2

Methyl {4,6-diamino-2-[5-fluoro-1-(2-fluorobenzyl)-1H-pyrazolo[3,4-b]pyridin-3-yl]pyrimidin-5-yl}methylcarbamate

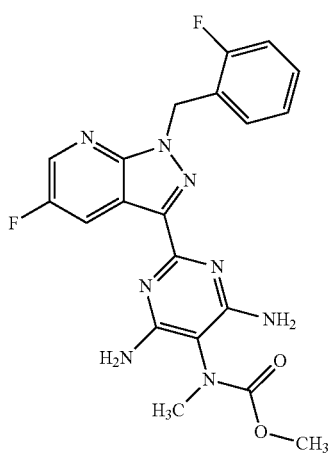 [SMILES: COC(=O)N(C)c1c(N)nc(-c2nn(Cc3ccccc3F)c3ncc(F)cc23)nc1N]

A quantity of 200 mg (0.469 mmol) of methyl 4,6-diamino-2-[5-fluoro-1-(2-fluorobenzyl)-1H-pyrazolo[3,4-b]pyridin-3-yl]pyrimidin-5-ylcarbamate (Example 1) was introduced in THF (5 ml) at 0° C. Then 0.704 ml (0.704 mmol) of lithium hexamethyldisilazane solution (1M in THF) was added and the mixture was stirred at this temperature for 20 min. Subsequently 43.8 µl (0.704 mmol) of iodomethane were added and the mixture was warmed to RT. After 1 h at this temperature, reaction was terminated with water (1 ml) and the reaction mixture was concentrated, the residue being separated by means of preparative RP-HPLC (water (+0.05% formic acid)-acetonitrile gradient).

Yield: 90 mg (44% of theory)
LC-MS (method 2): R$_t$=0.85 min
MS (ESIpos): m/z=441 (M+H)$^+$ $^1$H NMR (400 MHz, DMSO-d$_6$): δ=3.00 (s, 3H), 3.53 and 3.66 (2s, 3H), 5.81 (s, 2H), 6.57 (br. s, 4H), 7.13 (m, 2H), 7.22 (m, 1H), 7.35 (m, 1H), 8.67 (m, 1H), 8.87 (dd, 1H).

Example 3

Methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate

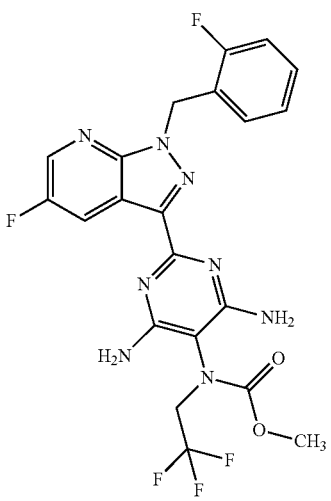 [SMILES: COC(=O)N(CC(F)(F)F)c1c(N)nc(-c2nn(Cc3ccccc3F)c3ncc(F)cc23)nc1N]

A quantity of 3.470 g (8.138 mmol) of the compound from Example 1 was suspended in 35 ml of THF, admixed at 0° C. with 358 mg (8.952 mmol) of sodium hydride (60% suspension in mineral oil) and stirred at 0° C. for 90 min, in the course of which a solution was formed. A quantity of 2.519 g (8.952 mmol) of 2,2,2-trifluoroethyl trichloromethanesulphonate was added and the mixture was stirred at RT for 48 h. It was then stirred with water and concentrated on a rotary evaporator. The residue was taken up in ethyl acetate, and the organic phase was washed twice with water and dried over sodium sulphate. This gave 5.005 g of the target compound (79% of theory, purity by HPLC 65%). A quantity of 250 mg of the residue was purified by means of preparative HPLC (mobile phase: methanol/water, gradient 30:70→90:10).

LC-MS (method 2): R$_t$=0.97 min; MS (EIpos): m/z=509 (M+H)$^+$.

¹H NMR (400 MHz, DMSO-d₆): δ [ppm]=3.63 (s, 3H), 4.06-4.15 (m, 2H), 5.80 (s, 2H), 6.46 (br s, 4H) 7.11-7.15 (m, 2H), 7.20-7.25 (m, 1H), 7.33-7.38 (m, 1H), 8.66 (dd, 1H), 8.91 (dd, 1H).

Example 4

Methyl {4,6-diamino-2-[5-fluoro-1-(2-fluorobenzyl)-1H-pyrazolo[3,4-b]pyridin-3-yl]pyrimidin-5-yl}carbamate hydrochloride

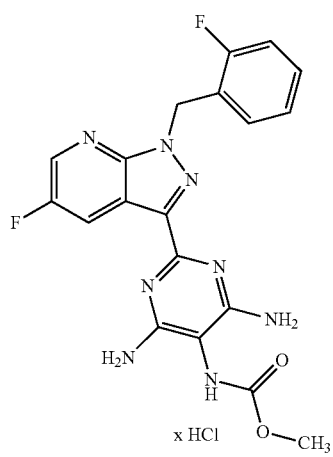 [SMILES: COC(=O)Nc1c(N)nc(-c2nn(Cc3ccccc3F)c3ncc(F)cc23)nc1N]

A solution of 100 mg (0.235 mmol) of Example 1 in 2 ml of 1,4-dioxane was prepared in a brown 5 ml glass bottle. In succession, 2 ml of isopropanol and 235 μl (0.235 mmol) of 1M hydrochloric acid were added to this solution, and the solution was stirred at RT until the solvents had evaporated. Air-drying gave 102 mg (94% of theory) of the title compound.

PLM (100×): crystalline
DSC: 224° C. (dec., ΔH=189 J/g)
TGA: 1% weight loss at 80° C.
LC-MS (method 3): R$_t$=0.91 min
MS (ESIpos): m/z=427 (M+H)⁺
¹H NMR (400 MHz, DMSO-d₆): δ [ppm]=3.35 and 3.65 (2 s, 3H), 5.92 (s, 2H), 7.15 (dd, 1H), 7.25 (m, 2H), 7.37 (m, 1H), 7.75 (br s, 4H), 8.08 and 8.39 (2 s, 1H), 8.82 (m, 2H), 13.2 (br s, 1H).
Elemental analysis for C₁₉H₁₆F₂N₈O₂+HCl:
calculated: % C, 49.31; % H, 3.70; % N, 24.21;
measured: % C, 49.5; % H, 3.7; % N, 24.3.

Example 5

Methyl {4,6-diamino-2-[5-fluoro-1-(2-fluorobenzyl)-1H-pyrazolo[3,4-b]pyridin-3-yl]pyrimidin-5-yl}carbamate sulphate

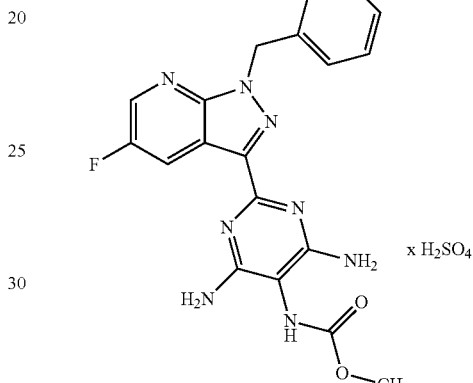

A solution of 100 mg (0.235 mmol) of Example 1 in 2 ml of 1,4-dioxane was prepared in a brown 5 ml glass bottle. In succession, 2 ml of isopropanol and a solution of 938 μl (0.235 mmol) of 0.25M sulphuric acid were added to this solution, and the solution was stirred at RT until the solvents had evaporated. Air-drying gave 103 mg (83.7% of theory) of the title compound.

PLM (100×): crystalline
DSC: 242° C. (dec., ΔH=115 J/g)
TGA: no weight loss prior to decomposition
LC-MS (method 3): R$_t$=0.91 min
MS (ESIpos): m/z=427 (M+H)⁺
¹H NMR (400 MHz, DMSO-d₆): δ [ppm]=3.56 and 3.66 (2 s, 3H), 5.93 (s, 2H), 7.16 (m, 2H), 7.25 (dd, 1H), 7.38 (m, 1H), 7.59 (br s, 4H), 8.03 and 8.32 (2 s, 1H), 8.82 (m, 2H), 13.0 (br s, 1H).
Elemental analysis for C₁₉H₁₆F₂N₈O₂+H₂SO₄:
calculated: % C, 43.51; % H, 3.46; % N, 21.37;
measured: % C, 43.6; % H, 3.4; % N, 21.2.

Example 6

Methyl {4,6-diamino-2-[5-fluoro-1-(2-fluorobenzyl)-1H-pyrazolo[3,4-b]pyridin-3-yl]pyrimidin-5-yl}carbamate phosphate

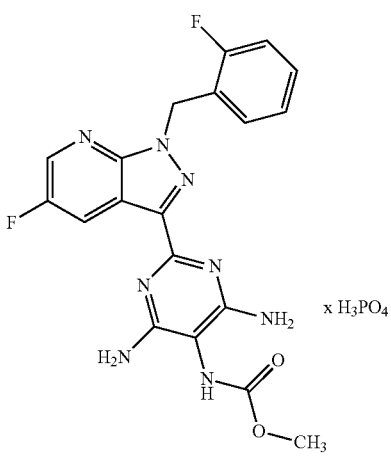 [SMILES: COC(=O)Nc1c(N)nc(-c2nn(Cc3ccccc3F)c3ncc(F)cc23)nc1N]

A solution of 100 mg (0.235 mmol) of Example 1 in 2 ml of 1,4-dioxane was prepared in a brown 5 ml glass bottle. In succession, 2 ml of THF and a solution of 16 μl (0.235 mmol) of 85% strength phosphoric acid in 0.3 ml of water were added to this solution, and the solution was stirred at RT until the solvents had evaporated. Air-drying gave 105 mg (85.4% of theory) of the title compound.

PLM (100×): crystalline
DSC: 183° C. (dec., ΔH=65 J/g)
TGA: 6% weight loss prior to decomposition
LC-MS (method 3): $R_t$=0.91 min
MS (ESIpos): m/z=427 (M+H)$^+$
$^1$H NMR (400 MHz, DMSO-d$_6$): δ [ppm]=3.57 and 3.62 (2 s, methyl signal obscured by water signal, 3H), 5.79 (s, 2H), 6.22 (br s, 4H), 7.15 (m, 2H), 7.22 (dd, 1H), 7.36 (m, 1H), 7.67 and 7.99 (2 s, 1H), 8.66 (m, 1H), 8.90 (m, 1H).
$^{31}$P-NMR (400 MHz, DMSO-d$_6$): δ [ppm]=−1.1
Elemental analysis for $C_{19}H_{16}F_2N_8O_2+H_3PO_4+2\ H_2O$:
calculated: % C, 40.72; % H, 4.14; % N, 19.99;
measured: % C, 40.5; % H, 4.0; % N, 19.5.

Example 7

Methyl {4,6-diamino-2-[5-fluoro-1-(2-fluorobenzyl)-1H-pyrazolo[3,4-b]pyridin-3-yl]pyrimidin-5-yl}carbamate mesylate

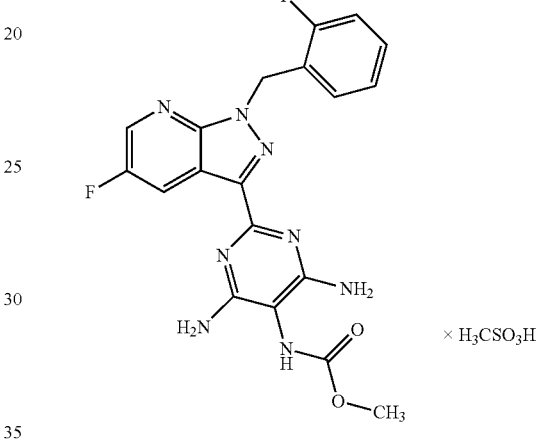

A solution of 100 mg (0.235 mmol) of Example 1 in 2 ml of 1,4-dioxane was prepared in a brown 5 ml glass bottle. In succession, 2 ml of ethanol and a solution of 22.5 mg (0.235 mmol) of methanesulphonic acid in 0.3 ml of water were added to this solution, and the solution was stirred at RT until the solvents had evaporated. Air-drying gave 103 mg (84% of theory) of the title compound.

PLM (100×): crystalline
DSC: 154° C. (ΔH=11.7 J/g), 167° C. (ΔH=−5 J/g), 215.2° C. (dec, ΔH=56.1 J/g)
TGA: gradual weight loss during the measurement
LC-MS (method 3): $R_t$=0.91 min
MS (ESIpos): m/z=427 (M+H)$^+$
$^1$H NMR (400 MHz, DMSO-d$_6$): δ [ppm]=2.31 (s, 3H), 3.57 and 3.66 (2 s, 3H), 5.93 (s, 2H), 7.17 (m, 2H), 7.25 (dd, 1H), 7.39 (m, 1H), 7.66 (s br, 4H), 8.06 and 8.34 (2 s, 1H), 8.81 (dd, 1H), 8.83 (s, 1H), 13.0 (br s, 1H).
Elemental analysis for $C_{19}H_{16}F_2N_8O_2+CH_4O_3S+H_2O$:
calculated: % C, 44.44; % H, 4.14; % N, 20.7;
measured: % C, 44.3; % H, 4.1; % N, 20.2.

Example 8

Methyl {4,6-diamino-2-[5-fluoro-1-(2-fluorobenzyl)-1H-pyrazolo[3,4-b]pyridin-3-yl]pyrimidin-5-yl}carbamate ethane-1,2-disulphonate

Example 9

Methyl {4,6-diamino-2-[5-fluoro-1-(2-fluorobenzyl)-1H-pyrazolo[3,4-b]pyridin-3-yl]pyrimidin-5-yl}carbamate maleate

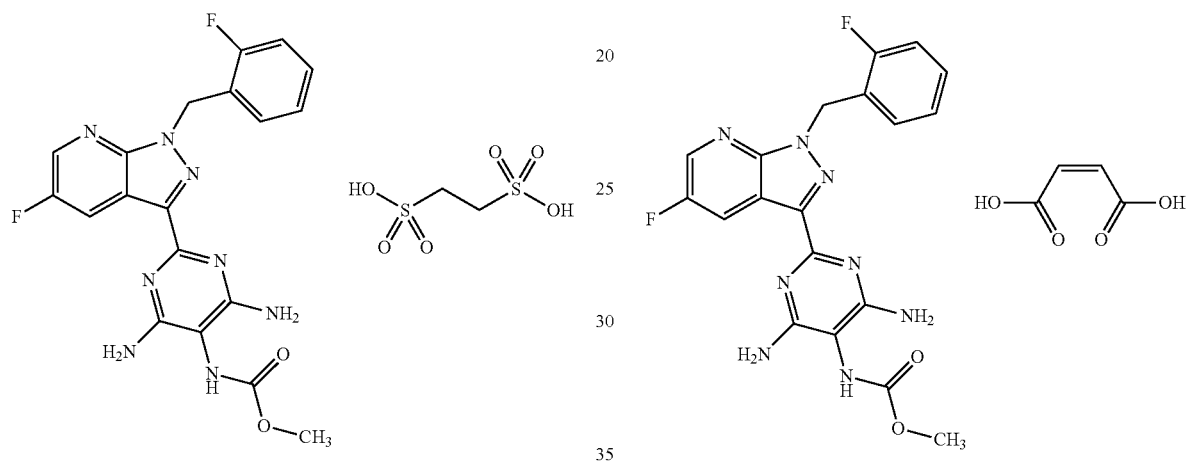

A solution of 100 mg (0.235 mmol) of Example 1 in 2 ml of 1,4-dioxane was prepared in a brown 5 ml glass bottle. In succession, 2 ml of isopropanol and 44.6 mg (0.235 mmol) of ethane-1,2-disulphonic acid were added to this solution, and the solution was stirred at RT until the solvents had evaporated. Air-drying gave 111 mg (73.7% of theory) of the title compound.

PLM (100×): predominantly crystalline
DSC: 97° C. (dec., ΔH=103 J/g)
TGA: gradual weight loss during the measurement
LC-MS (method 3): $R_t$=0.90 min
MS (ESIpos): m/z=427 (M+H)$^+$
$^1$H NMR (400 MHz, DMSO-$d_6$): δ [ppm]=2.66 (s, 4H), 3.57 and 3.66 (2 s, methyl signal obscured by water signal, 3H), 5.93 (s, 2H), 7.17 (m, 2H), 7.25 (m, 1H), 7.39 (m, 1H), 8.05 and 8.35 (2 s, 1H), 8.80 (dd, 1H), 8.84 (s, 1H).

Elemental analysis for $C_{19}H_{16}F_2N_8O_2+C_2H_6O_6S_2+0.25\ H_2O_2+0.25\ C_4H_8O_2$:
calculated: % C, 41.09; % H, 3.84; % N, 17.42;
measured: % C, 41.2; % H, 4.2; % N, 17.6.

A solution of 100 mg (0.235 mmol) of Example 1 in 2 ml of 1,4-dioxane was prepared in a brown 5 ml glass bottle. In succession, 2 ml of isopropanol and 27.2 mg (0.235 mmol) of maleic acid were added to this solution, and the solution was stirred at RT until the solvents had evaporated. Air-drying gave 108 mg (84.9% of theory) of the title compound.

PLM (100×): crystalline
DSC: 192° C. (dec., ΔH=173 J/g)
TGA: 3% weight loss prior to decomposition
LC-MS (method 3): $R_t$=0.91 min
MS (ESIpos): m/z=427 (M+H)$^+$
$^1$H NMR (400 MHz, DMSO-$d_6$): δ [ppm]=3.56 and 3.64 (2 s, obscured by dioxane signal, 3H), 5.85 (s, 2H), 6.16 (s, 2H), 6.9 (br s, 4H), 7.15 (m, 2H), 7.23 (dd, 1H), 7.37 (m, 1H), 7.85 and 8.13 (2 s, 1H), 8.73 (s, 1H), 8.86 (dd, 1H).

Elemental analysis for $C_{19}H_{16}F_2N_8O_2+C_4H_4O_4+0.5\ H_2O_2+0.5\ C_4H_8O_2$:
calculated: % C, 50.42; % H, 4.23; % N, 18.82;
measured: % C, 50.7; % H, 3.9; % N, 18.8.

Example 10

Methyl {4,6-diamino-2-[5-fluoro-1-(2-fluorobenzyl)-1H-pyrazolo[3,4-b]pyridin-3-yl]pyrimidin-5-yl}carbamate nitrate

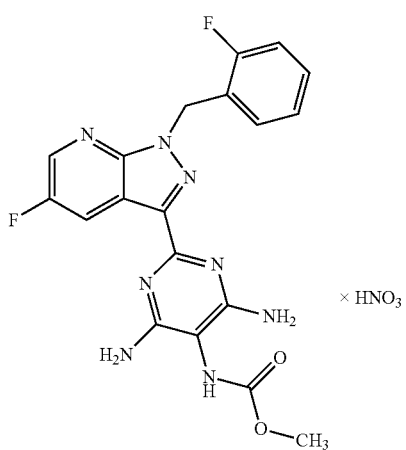 [SMILES: COC(=O)Nc1c(N)nc(-c2nn(Cc3ccccc3F)c3ncc(F)cc23)nc1N]

A solution of 100 mg (0.235 mmol) of Example 1 in 2 ml of isopropanol was prepared in a brown 5 ml glass bottle. In succession, 2 ml of isopropanol and 0.235 μl (0.235 mmol) of 1M nitric acid were added to this solution, and the solution was stirred at RT until the solvents had evaporated. Air-drying gave 103 mg (89.7% of theory) of the title compound.

PLM (100×): crystalline
DSC: 175° C. (dec., ΔH=−224 J/g)
TGA: 3% weight loss prior to decomposition
LC-MS (method 3): $R_t$=0.91 min
MS (ESIpos): m/z=427 (M+H)$^+$
$^1$NMR (400 MHz, DMSO-d$_6$): δ [ppm]=3.57 and 3.66 (2 s, 3H), 5.93 (s, 2H), 7.16 (m, 2H), 7.25 (dd, 1H), 7.38 (m, 1H), 7.65 (br s, 4H), 8.02 and 8.32 (2 s, 1H), 8.80 (dd, 1H), 8.83 (s, 1H), 13.0 (br s, 1H).

Elemental analysis for $C_{19}H_{16}F_2N_8O_2$+HNO$_3$+0.75 H$_2$O:
calculated: % C, 45.38; % H, 3.71; % N, 25.07;
measured: % C, 45.4; % H, 3.7; % N, 25.0.

B. Assessment of Pharmacological Activity

The pharmacological effect of the compounds according to the invention can be shown in the following assays:

B-1. Vasorelaxant Effect In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The force of contraction is detected with Statham UC2 cells, amplified and digitized via A/D converters (DAS-1802 HC, Keithley Instruments, Munich) and recorded in parallel on chart recorders. To produce a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. The concentration necessary to reduce the height of the control value by 50% is calculated from this (IC$_{50}$ value). The standard administration volume is 5 μl and the proportion of DMSO in the bath solution corresponds to 0.1%.

Representative IC$_{50}$ values for the compounds according to the invention are shown in the table below (Table 1):

TABLE 1

| Example No. | IC$_{50}$ [nM] |
|---|---|
| 1 | 958 |
| 2 | 251 |
| 3 | 515 |

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative values (MEC=minimum effective concentration) for the compounds according to the invention are shown in the table below (Table 2):

TABLE 2

| Example No. | MEC [μM] |
|---|---|
| 1 | 0.3 |
| 2 | 0.1 |
| 3 | 0.03 |

B-3. Radiotelemetric Measurement of Blood Pressure on Conscious Spontaneously Hypertensive Rats A commercially available telemetry system from DATA SCIENCES INTERNATIONAL DSI, USA, is employed for the blood pressure measurements on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motions of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6.00 am and at 7.00 pm.

Transmitter Implantation

The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed.

An antibiotic (Tardomyocel COMP, Bayer, 1 ml/kg s.c.) is administered postoperatively for prophylaxis of infection.

Substances and Solutions

Unless indicated otherwise, the substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight.

A solvent-treated group of animals is employed as control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case:

systolic blood pressure (SBP)

diastolic blood pressure (DBP)

mean arterial pressure (MAP)

heart rate (HR)

activity (ACT).

The acquisition of measured values is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9.00 am on the day of the experiment. Following the administration, the parameters described above are measured over 24 hours.

Evaluation

After the end of the experiment, the acquired individual data are sorted using the analysis software (Dataquest™ A.R.T.™ Analysis). The blank value is assumed to be the time 2 hours before administration of the substance, so that the selected data set includes the period from 7.00 am on the day of the experiment to 9.00 am on the following day.

The data are smoothed over a presettable time by determination of the average (15-minute average) and transferred as a text file to a storage medium. The measured values presorted and compressed in this way are transferred into Excel templates and tabulated. For each day of the experiment, the data obtained are stored in a dedicated file carrying the number of the experiment. Results and test protocols are filed in paper form sorted by numbers.

Representative values for the compounds according to the invention are shown in the table below (Table 3):

TABLE 3

| | Example 1: | | | | Example 2: | |
|---|---|---|---|---|---|---|
| hours after substance administration | Vehicle mean blood pressure (mm Hg) | Dosage 0.3 mg/kg p.o. mean blood pressure (mm Hg) | Dosage 3.0 mg/kg p.o. mean blood pressure (mm Hg) | hours after substance administration | Vehicle mean blood pressure (mm Hg) | Dosage 0.3 mg/kg p.o. mean blood pressure (mm Hg) |
| 0 | 153.6 | 151.0 | 149.0 | 0 | 149.0 | 161.3 |
| 1 | 164.5 | 148.4 | 129.3 | 1 | 158.2 | 145.7 |
| 2 | 146.7 | 136.4 | 111.1 | 2 | 142.2 | 130.5 |
| 3 | 145.4 | 130.6 | 106.0 | 3 | 149.2 | 121.5 |
| 4 | 149.6 | 129.1 | 107.8 | 4 | 152.3 | 123.1 |
| 5 | 149.9 | 132.8 | 109.3 | 5 | 155.8 | 121.6 |
| 6 | 151.6 | 125.6 | 106.8 | 6 | 147.3 | 123.8 |
| 7 | 147.6 | 131.9 | 110.9 | 7 | 147.3 | 124.4 |
| 8 | 147.5 | 131.8 | 109.8 | 8 | 149.3 | 128.7 |
| 9 | 150.8 | 138.5 | 114.3 | 9 | 151.0 | 133.7 |
| 10 | 149.8 | 138.3 | 114.5 | 10 | 152.5 | 139.2 |
| 11 | 154.0 | 138.9 | 115.6 | 11 | 150.3 | 137.9 |
| 12 | 145.3 | 137.7 | 118.8 | 12 | 146.2 | 143.0 |
| 13 | 141.1 | 142.9 | 120.4 | 13 | 143.2 | 146.0 |
| 14 | 147.8 | 144.5 | 122.8 | 14 | 146.4 | 149.2 |
| 15 | 151.0 | 143.8 | 125.8 | 15 | 150.5 | 152.3 |
| 16 | 151.3 | 146.3 | 131.5 | 16 | 145.3 | 155.5 |
| 17 | 148.8 | 141.8 | 124.7 | 17 | 143.9 | 156.3 |
| 18 | 149.2 | 138.4 | 129.6 | 18 | 150.3 | 157.3 |
| 19 | 151.2 | 149.2 | 135.6 | 19 | 147.7 | 156.9 |
| 20 | 152.6 | 145.1 | 135.2 | 20 | 153.4 | 156.3 |
| 21 | 146.3 | 142.1 | 129.3 | 21 | 148.6 | 149.3 |
| 22 | 146.3 | 141.8 | 128.3 | 22 | 153.3 | 147.1 |

TABLE 3-continued

| | Example 1: | | | Example 2: | | |
|---|---|---|---|---|---|---|
| hours after substance administration | Vehicle mean blood pressure (mm Hg) | Dosage 0.3 mg/kg p.o. mean blood pressure (mm Hg) | Dosage 3.0 mg/kg p.o. mean blood pressure (mm Hg) | hours after substance administration | Vehicle mean blood pressure (mm Hg) | Dosage 0.3 mg/kg p.o. mean blood pressure (mm Hg) |
| 23 | 150.3 | 143.6 | 130.2 | 23 | 151.1 | 153.1 |
| 24 | 147.4 | 135.1 | 130.8 | 24 | 154.1 | 152.3 |

REFERENCES

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-4. Determination of Pharmacokinetic Parameters Following Intravenous and Peroral Administration:

The pharmacokinetic parameters of the substance are determined in male CD-1 mice, male Wistar rats and female beagles. The administration volume is 10 ml/kg for mice, 5 ml/kg for rats and 0.5 ml/kg for dogs. Intravenous administration is via a formulation of species-specific plasma/DMSO (99/1) in the case of mice and rats and via water/PEG400/ethanol (50/40/10) in the case of dogs. For easier removal of blood, a silicone catheter is inserted into the right Vena jugularis externa of the rats before the administration of substance. The surgical intervention takes place one day prior to the experiment with isofluran anaesthesia and administration of an analgetic (atropine/rimadyl (3/1) 0.1 ml s.c.). Substance administration is as i.v. bolus in the case of mice, as i.v. bolus or via a 15-minute infusion in the case of rats and via a 15-minute infusion in the case of dogs. Removal of blood is after 0.033, 0.083, 0.17, 0.5, 1, 2, 3, 4, 6, 7 and 24 hours in the case of mice and, after a 15-minute infusion, after 0.083, 0.25, 0.28 0.33, 0.42, 0.75, 1, 2, 3, 4, 6, 7 and 24 hours in the case of dogs and rats and after an i.v. bolus administration, after 0.033, 0.083, 0.17, 0.5, 1, 2, 3, 4, 6, 7 and 24 hours in the case of rats. For all species, oral administration of the dissolved substance via gavage is carried out based on a water/PEG400/ethanol formulation (50/40/10). Here, the removal of blood from rats and dogs is after 0.083, 0.17, 0.5, 0.75, 1, 2, 3, 4, 6, 7 and 24 hours. The blood is removed into heparinized tubes. The blood plasma is then obtained by centrifugation; if required, it can be stored at −20° C. until further processing.

An internal standard (ZK 228859) is added to the unknown samples, calibration samples and QCs, and the protein is precipitated using excess acetonitrile. After addition of an ammonium acetate buffer (0.01 M, pH 6.8 (Example 1/3) or pH 3.0 (Example 2)) and subsequent vortexing, the mixture is centrifuged at 1000 g and the supernatant is examined by LC-MS/MS (API 4000, AB Sciex). Chromatographic separation is carried out on an Agilent 1100-HPLC. The injection volume is 10 µl. The separation column used is a Phenomenex Luna 5µ C8(2) 100A 50×2 mm, adjusted to a temperature of 40° C. For Example 1, a binary mobile phase gradient at 400 µl/min is used (A: 0.01M ammonium acetate buffer pH 6.8, B: 0.1% formic acid in acetonitrile): 0 min (90% A), 1 min (90% A), 3.5 min (15% A), 4.5 min (15% A), 4.6 min (90% A), 7 min (90% A). For Example 2, a binary mobile phase gradient at 500 µl/min is used instead (A: 0.01M ammonium acetate buffer pH 3.0, B: 0.1% formic acid in acetonitrile): 0 min (90% A), 1.5 min (90% A), 3.5 min (10% A), 4.5 min (10% A), 5 min (90% A), 7 min (90% A). For Example 3, a binary mobile solvent gradient at 500 µl/min is used instead (A: 0.01M ammonium acetate buffer pH 6.8, B: 0.1% formic acid in acetonitrile): 0 min (90% A), 1 min (90% A), 3 min (10% A), 4 min (10% A), 4.5 min (90% A), 6 min (90% A). The temperature of the Turbo V ion source is 500° C. The following MS instrument parameters are used: curtain gas 20 units (Example 1), 16 units (Example 2) or 15 units (Example 3), ion spray voltage 5 kV (Example 1/2) or 4.5 units (Example 3), gas 1 35 units (Example 1/3) or 25 units (Example 2), gas 2 30 units, CAD gas 4 units (Example 1/3) or 3 units (Example 2). The substances are quantified by peak heights or areas using extracted ion chromatograms of specific MRM experiments.

The plasma concentration/time plots determined are used to calculate the pharmacokinetic parameters such as AUC, $C_{max}$, MRT (mean residence time), $t_{1/2}$ (half life) and CL (clearance) employing the validated pharmacokinetic calculation programs KinEx (Vers. 2.5 and 3).

As the substance quantification is carried out in plasma, it is necessary to determine the blood/plasma distribution of the substance to be able to adjust the pharamacokinetic parameters in an appropriate manner To this end, a defined amount of substance is incubated in heparinized whole blood of the species in question in a rocking roller mixer for 20 min. After centrifugation at 1000 g, the plasma concentration is measured (see above) and determined by calculating the quotient of the $c_b/c_p$ values.

Following intravenous administration of 0.3 mg/kg of the compounds according to the invention in rats, the following values were recorded:

| Example | 1.* | 2.** | 3.** |
|---|---|---|---|
| $AUC_{norm}$ [kg · h/l] | 4.36 | 1.79 | 1.36 |
| $CL_{blood}$ [lh/kg] | 0.29 | 0.53 | 1.02 |
| MRT [h] | 4.1 | 2.3 | 2.3 |
| $t_{1/2}$ [h] | 3.4 | 1.7 | 1.9 |

*15-minute infusion

**i.v. bolus administration

49

B-5. Safety Profile

The substances according to the invention show a surprisingly favourable safety profile in vivo which was established by non-clinical safety studies according to OECD (OECD guidelines for testing of chemicals, No. 407) and ICH (3BS2A) guidelines.

C. Working Examples for Pharmaceutical Compositions

The compounds according to the invention can be converted to pharmaceutical formulations as follows Tablet:

Composition:

100 mg of the compound according to the invention, 50 mg of lactose (monohydrate), 50 mg of maize starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Preparation:

The mixture of the compound according to the invention, lactose and starch is granulated with a 5% solution (w/w) of the PVP in water. After drying, the granules are mixed with the magnesium stearate for 5 minutes. This mixture is pressed with a conventional tableting press (for tablet dimensions see above). The guide value used for the pressing is a pressing force of 15 kN.

Suspension for Oral Administration:

Composition:

1000 mg of the compound according to the invention, 1000 mg of ethanol (96%), 400 mg of Rhodigel® (xanthan gum from FMC, Pennsylvania, USA) and 99 g of water.

A single dose of 100 mg of the compound according to the invention corresponds to 10 ml of oral suspension.

Preparation:

The Rhodigel is suspended in ethanol and the compound according to the invention is added to the suspension. The water is added while stirring. The mixture is stirred for approx. 6 h until swelling of the Rhodigel has ended.

Solution for Oral Administration:

Composition:

500 mg of the compound according to the invention, 2.5 g of polysorbate and 97 g of polyethylene glycol 400. A single dose of 100 mg of the compound according to the invention corresponds to 20 g of oral solution.

Preparation:

The compound according to the invention is suspended in the mixture of polyethylene glycol and polysorbate while stirring. The stirring operation is continued until dissolution of the compound according to the invention is complete.

i.v. Solution:

The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

50

The invention claimed is:
1. A compound of formula (I)

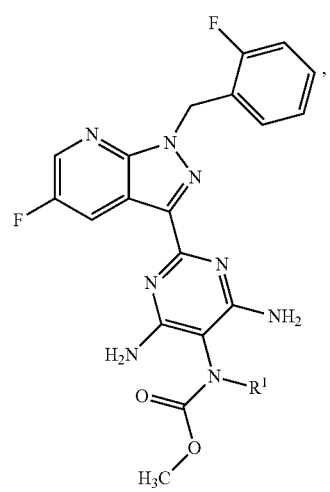

in which
R$^1$ represents hydrogen or (C$_1$-C$_4$)-alkyl,
where (C$_1$-C$_4$)-alkyl may be substituted by one or two substituents independently of one another selected from the group consisting of fluorine and trifluoromethyl,
and their N-oxides, salts, and salts of the N-oxides.

2. The compound of the formula (I) according to claim 1 in which
R$^1$ represents hydrogen or methyl,
where methyl may be substituted by a trifluoromethyl substituent,
and salts thereof.

3. The compound of the formula (I) according to claim 1, selected from the group consisting of:
methyl {4,6-diamino-2-[5-fluoro-1-(2-fluorobenzyl)-1H-pyrazolo[3,4-b]pyridin-3-yl]pyrimidin-5-yl}carbamate;
methyl {4,6-diamino-2-[5-fluoro-1-(2-fluorobenzyl)-1H-pyrazolo[3,4-b]pyridin-3-yl]pyrimidin-5-yl}methylcarbamate;
methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate;
methyl {4,6-diamino-2-[5-fluoro-1-(2-fluorobenzyl)-1H-pyrazolo[3,4-b]pyridin-3-yl]pyrimidin-5-yl}carbamate hydrochloride;
methyl {4,6-diamino-2-[5-fluoro-1-(2-fluorobenzyl)-1H-pyrazolo[3,4-b]pyridin-3-yl]pyrimidin-5-yl}carbamate sulphate;
methyl {4,6-diamino-2-[5-fluoro-1-(2-fluorobenzyl)-1H-pyrazolo[3,4-b]pyridin-3-yl]pyrimidin-5-yl}carbamate phosphate;
methyl {4,6-diamino-2-[5-fluoro-1-(2-fluorobenzyl)-1H-pyrazolo[3,4-b]pyridin-3-yl]pyrimidin-5-yl}carbamate mesylate;
methyl {4,6-diamino-2-[5-fluoro-1-(2-fluorobenzyl)-1H-pyrazolo[3,4-b]pyridin-3-yl]pyrimidin-5-yl}carbamate ethane-1,2-disulphonate;
methyl {4,6-diamino-2-[5-fluoro-1-(2-fluorobenzyl)-1H-pyrazolo[3,4-b]pyridin-3-yl]pyrimidin-5-yl}carbamate maleate; and methyl {4,6-diamino-2-[5-fluoro-1-(2-fluorobenzyl)-1H-pyrazolo[3,4-b]pyridin-3-yl]pyrimidin-5-yl}carbamate nitrate.

4. A process for preparing a compound of claim 1, wherein a compound of the formula (II)

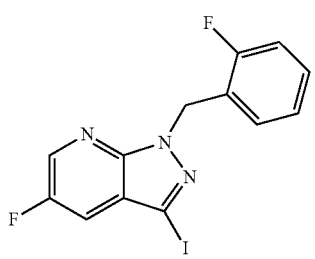

(II)

[A] is reacted in an inert solvent in the presence of hexabutyltin and a suitable palladium catalyst with intermediate formation of a tin species with the compound of the formula (III)

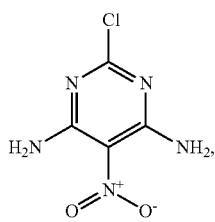

(III)

to give the compound of the formula (IV)

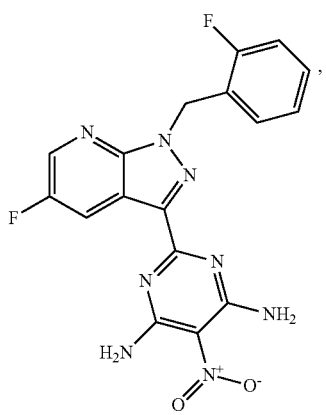

(IV)

this is then reduced in an inert solvent with a suitable reducing agent to give the compound of the formula (V)

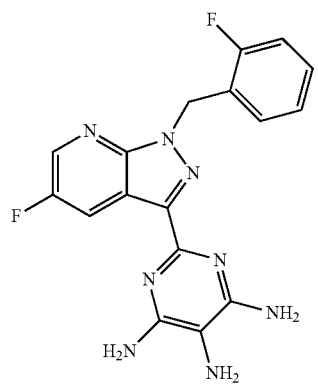

(V)

and this is then reacted in the presence of a suitable base in the presence or absence of a solvent with methyl chloroformate to give the compound of the formula (I-A)

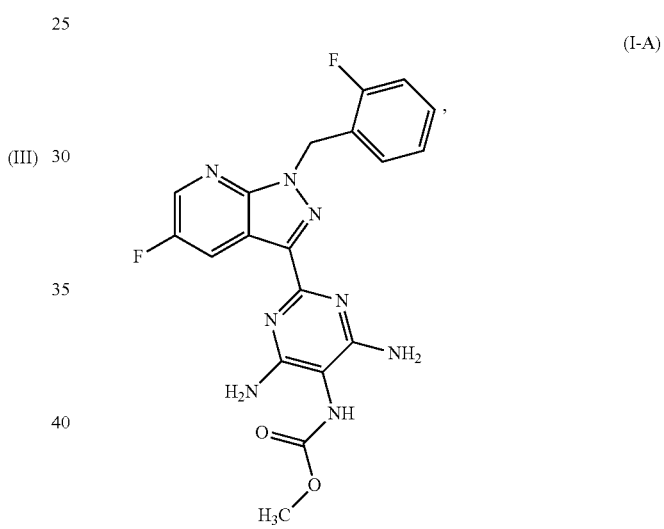

(I-A)

or

[B] the compound of the formula (II) is reacted in an inert solvent with copper cyanide to give the compound of the formula (VI)

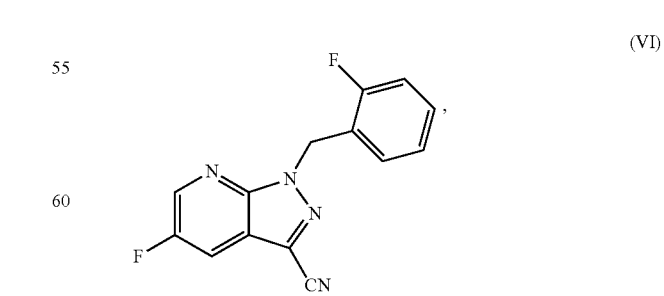

(VI)

this is then, under acidic conditions, converted into the compound of the formula (VII)

(VII)

[Structure: 1-(2-fluorobenzyl)-5-fluoro-1H-pyrazolo[3,4-b]pyridine-3-carboxamidine · H₃CCO₂H]

this is subsequently reacted in an inert solvent in the presence of a suitable base with the compound of the formula (VIII)

(VIII)

[Structure: NC-CH(CN)-N=N-phenyl]

to give the compound of the formula (IX)

(IX)

[Structure: pyrazolopyridine-pyrimidine intermediate with phenylazo group]

and this is then reduced in an inert solvent in the presence of a suitable reducing agent to give the compound (V), and this is subsequently reacted further according to process [A] to give compound (I-A), or

[C] the compound of the formula (I-A) is reacted in an inert solvent in the presence of a suitable base with a compound of the formula (X)

$R^{14}-X^1$ (X), in which
$R^{14}$ represents (C₁-C₄)-alkyl, where (C₁-C₄)-alkyl may be substituted by one or two substituents independently of one another selected from the group consisting of fluorine and trifluoromethyl, and $X^1$ represents a leaving group such as, for example, halogen, in particular bromine or iodine, trichloromethanesulphonate, mesylate or tosylate to give a compound of the formula (I-B)

(I-B)

[Structure of compound I-B]

in which $R^{14}$ has the meaning given above, and the resulting compounds of the formulae (I-A) and (I-B) are, where appropriate, converted with the appropriate (i) solvents and/or (ii) acids or bases into their solvates, salts and/or solvates of the salts.

5. A pharmaceutical formulation comprising a compound of claim 1 and an inert, non-toxic, pharmaceutically suitable excipient.

6. A pharmaceutical composition comprising a compound of claim 1 and a further active compound selected from the group consisting of an organic nitrate, an NO donor, a cGMP-PDE inhibitor, an agent having antithrombotic activity, an agent for lowering blood pressure, and an agent for altering lipid metabolism.

7. A compound of the formula:

[Structure of final compound]

or a salt thereof.

* * * * *